United States Patent
Shang et al.

(10) Patent No.: US 11,517,428 B2
(45) Date of Patent: Dec. 6, 2022

(54) TRANSCATHETER PULMONIC REGENERATIVE VALVE

(71) Applicant: Edwards Lifesciences Corporation, Irvine, CA (US)

(72) Inventors: Hao Shang, Fullerton, CA (US); Louis A. Campbell, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 268 days.

(21) Appl. No.: 16/666,319

(22) Filed: Oct. 28, 2019

(65) Prior Publication Data
US 2020/0138573 A1   May 7, 2020

Related U.S. Application Data

(60) Provisional application No. 62/754,102, filed on Nov. 1, 2018.

(51) Int. Cl.
*A61F 2/24*   (2006.01)
*A61L 27/36*   (2006.01)
(Continued)

(52) U.S. Cl.
CPC .......... *A61F 2/2418* (2013.01); *A61F 2/2433* (2013.01); *A61F 2/2436* (2013.01);
(Continued)

(58) Field of Classification Search
CPC .... A61F 2/2418; A61F 2/2433; A61F 2/2436; A61F 2002/0081; A61F 2210/0004;
(Continued)

(56) References Cited

U.S. PATENT DOCUMENTS

| | | | |
|---|---|---|---|
| 2,393,580 | A | 1/1946 | Weiskopf |
| 4,120,649 | A | 10/1978 | Schechter |

(Continued)

FOREIGN PATENT DOCUMENTS

| | | |
|---|---|---|
| EP | 0169259 A1 | 1/1986 |
| EP | 2394673 A1 | 12/2011 |
| WO | 8401894 A1 | 5/1984 |
| WO | 9511047 A1 | 4/1995 |
| WO | 9522361 A1 | 8/1995 |
| WO | 9534332 A1 | 12/1995 |

(Continued)

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

(Continued)

*Primary Examiner* — Suzette J Gherbi
(74) *Attorney, Agent, or Firm* — Christian S. Hans; KPPB

(57) ABSTRACT

Artificial heart valves, their manufacture, and methods of use are described. Generally, artificial heart valves can be deployed to replace or supplement defective heart valves in a patient. These artificial heart valves can comprise a frame with an inner skirt and leaflets. These inner skirt and leaflets can be generated from regenerative tissue to allow integration of the tissue with the body of a patient, while the frame can be generated from bioabsorbable material to allow dissolution of the frame over time. This combination of materials may allow for the artificial valve to grow with a patient and avoid costly and potentially dangerous replacement for patients receiving artificial valves.

20 Claims, 31 Drawing Sheets

(51) Int. Cl.
- *A61L 27/54* (2006.01)
- *A61L 31/04* (2006.01)
- *A61L 31/14* (2006.01)
- *A61F 2/00* (2006.01)

(52) U.S. Cl.
CPC ........... *A61L 27/3633* (2013.01); *A61L 27/54* (2013.01); *A61L 31/041* (2013.01); *A61L 31/148* (2013.01); *A61F 2002/0081* (2013.01); *A61F 2210/0004* (2013.01); *A61F 2220/0008* (2013.01); *A61F 2250/001* (2013.01); *A61F 2250/0039* (2013.01); *A61F 2250/0067* (2013.01); *A61L 2430/20* (2013.01)

(58) Field of Classification Search
CPC ........ A61F 2220/0008; A61F 2250/001; A61F 2250/0039; A61F 2250/0067; A61L 27/3633; A61L 27/54; A61L 31/041; A61L 31/148; A61L 2430/20
USPC .................................................. 623/2.1–2.19
See application file for complete search history.

(56) References Cited

U.S. PATENT DOCUMENTS

| | | |
|---|---|---|
| 4,323,358 A | 4/1982 | Lentz |
| 4,350,492 A | 9/1982 | Wright |
| 4,372,743 A | 2/1983 | Lane |
| 4,378,224 A | 3/1983 | Nimni |
| 4,402,697 A | 9/1983 | Pollock et al. |
| 4,405,327 A | 9/1983 | Pollock |
| 4,481,009 A | 11/1984 | Nashef |
| 4,553,974 A | 11/1985 | Dewanjee |
| 4,624,822 A | 11/1986 | Arru et al. |
| 4,647,283 A | 3/1987 | Carpentier et al. |
| 4,648,881 A | 3/1987 | Carpentier et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,838,888 A | 6/1989 | Nashef |
| 4,865,871 A | 9/1989 | Livesey et al. |
| 4,885,005 A | 12/1989 | Nashef et al. |
| 4,958,008 A | 9/1990 | Petite et al. |
| 4,976,733 A | 12/1990 | Girardot |
| 5,002,566 A | 3/1991 | Carpentier et al. |
| 5,051,401 A | 9/1991 | Sikes |
| 5,080,670 A | 1/1992 | Imamura et al. |
| 5,094,661 A | 3/1992 | Levy et al. |
| 5,104,405 A | 4/1992 | Nimni |
| 5,116,564 A | 5/1992 | Jansen et al. |
| 5,147,514 A | 9/1992 | Mechanic |
| 5,154,007 A | 10/1992 | Piunno et al. |
| 5,200,399 A | 4/1993 | Wettlaufer et al. |
| 5,215,541 A | 6/1993 | Nashef et al. |
| 5,279,612 A | 1/1994 | Eberhardt |
| 5,329,846 A | 7/1994 | Bonutti |
| 5,397,353 A | 3/1995 | Oliver et al. |
| 5,437,287 A | 8/1995 | Phillips et al. |
| 5,447,536 A | 9/1995 | Girardot et al. |
| 5,460,962 A | 10/1995 | Kemp |
| 5,476,516 A | 12/1995 | Seifter et al. |
| 5,489,297 A * | 2/1996 | Duran ............... A61F 2/2418 623/2.13 |
| 5,509,932 A | 4/1996 | Keogh et al. |
| 5,558,875 A | 9/1996 | Wang |
| 5,595,571 A | 1/1997 | Jaffe et al. |
| 5,613,982 A | 3/1997 | Goldstein |
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,862,806 A | 1/1999 | Cheung |
| 5,873,812 A | 2/1999 | Ciana et al. |
| 5,899,936 A | 5/1999 | Goldstein |
| 5,911,951 A | 6/1999 | Girardot et al. |
| 5,919,472 A | 7/1999 | Trescony et al. |
| 5,921,980 A | 7/1999 | Kim |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rettenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Sirnionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,589,591 B1 | 7/2003 | Mansouri et al. |
| 6,605,667 B1 | 8/2003 | Badejo et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |

(56) References Cited

U.S. PATENT DOCUMENTS

| | | | |
|---|---|---|---|
| 6,682,559 B2 | 1/2004 | Myers et al. | |
| 6,696,074 B2 | 2/2004 | Dai et al. | |
| 6,734,018 B2 | 5/2004 | Wolfinbarger, Jr. et al. | |
| 6,753,181 B2 | 6/2004 | Atala | |
| 6,790,229 B1 | 9/2004 | Berreklouw | |
| 6,797,000 B2 | 9/2004 | Simpson et al. | |
| 6,872,226 B2 | 3/2005 | Cali et al. | |
| 6,878,168 B2 | 4/2005 | Carpentier et al. | |
| 6,908,591 B2 | 6/2005 | MacPhee et al. | |
| 6,911,043 B2 | 6/2005 | Myers et al. | |
| 6,919,172 B2 | 7/2005 | DePablo et al. | |
| 7,008,763 B2 | 3/2006 | Cheung | |
| 7,029,434 B2 | 4/2006 | Carpentier et al. | |
| 7,037,333 B2 | 5/2006 | Myers et al. | |
| 7,063,726 B2 | 6/2006 | Crouch et al. | |
| 7,078,163 B2 | 7/2006 | Torrianni | |
| 7,141,064 B2 | 11/2006 | Scott et al. | |
| 7,143,769 B2 | 12/2006 | Stoltz et al. | |
| 7,214,344 B2 | 5/2007 | Carpentier et al. | |
| 7,238,200 B2 | 7/2007 | Lee et al. | |
| 7,318,998 B2 | 1/2008 | Goldstein et al. | |
| 7,338,757 B2 | 3/2008 | Wolfinbarger, Jr. et al. | |
| 7,354,749 B2 | 4/2008 | Fisher et al. | |
| 7,367,969 B2 | 5/2008 | Stoltz et al. | |
| RE40,570 E | 11/2008 | Carpentier et al. | |
| 7,498,565 B2 | 3/2009 | Silberberg et al. | |
| 7,579,381 B2 | 8/2009 | Dove | |
| 7,594,974 B2 | 9/2009 | Cali et al. | |
| 7,648,676 B2 | 1/2010 | Mills et al. | |
| 7,682,304 B2 | 3/2010 | Heyninck-Jantz et al. | |
| 7,914,569 B2 | 3/2011 | Nguyen et al. | |
| 7,919,112 B2 | 4/2011 | Pathak et al. | |
| 7,972,376 B1 | 7/2011 | Dove et al. | |
| 8,007,992 B2 | 8/2011 | Tian et al. | |
| 8,038,708 B2 | 10/2011 | Case et al. | |
| 8,043,450 B2 | 10/2011 | Cali et al. | |
| 8,075,615 B2 | 12/2011 | Eberhardt et al. | |
| 8,105,375 B2 | 1/2012 | Navia et al. | |
| 8,136,218 B2 | 3/2012 | Millwee et al. | |
| 8,308,797 B2 | 11/2012 | Paniagua et al. | |
| 8,361,144 B2 | 1/2013 | Fish et al. | |
| 8,377,143 B2 | 2/2013 | Hamby et al. | |
| 8,475,827 B2 | 7/2013 | Hamby et al. | |
| 10,376,359 B2 * | 8/2019 | Essinger | A61F 2/2412 |
| 10,729,542 B2 * | 8/2020 | Howard | A61F 2/2412 |
| 2001/0000804 A1 | 5/2001 | Goldstein et al. | |
| 2001/0025196 A1 | 9/2001 | Chinn et al. | |
| 2001/0027344 A1 | 10/2001 | Bonutti | |
| 2001/0032024 A1 | 10/2001 | Cunanan et al. | |
| 2001/0039450 A1 * | 11/2001 | Pavcnik | A61F 2/01 623/1.36 |
| 2001/0039459 A1 | 11/2001 | Stone | |
| 2002/0001834 A1 | 1/2002 | Keogh et al. | |
| 2002/0091441 A1 | 7/2002 | Guzik | |
| 2002/0111532 A1 | 8/2002 | Pathak et al. | |
| 2003/0035843 A1 | 2/2003 | Livesey et al. | |
| 2003/0055496 A1 * | 3/2003 | Cai | A61F 2/2412 623/2.19 |
| 2003/0125805 A1 | 7/2003 | Johnson et al. | |
| 2003/0135284 A1 | 7/2003 | Crouch et al. | |
| 2003/0167089 A1 | 9/2003 | Lane | |
| 2003/0212454 A1 | 11/2003 | Scott et al. | |
| 2004/0030381 A1 | 2/2004 | Shu | |
| 2004/0086543 A1 | 5/2004 | Keogh et al. | |
| 2004/0158320 A1 | 8/2004 | Simionescu et al. | |
| 2005/0010773 A1 | 1/2005 | Lapstun et al. | |
| 2005/0119736 A1 | 6/2005 | Zilla et al. | |
| 2005/0136510 A1 | 6/2005 | Hendriks et al. | |
| 2005/0211680 A1 | 9/2005 | Li et al. | |
| 2006/0084957 A1 | 4/2006 | Delfyett et al. | |
| 2006/0099326 A1 | 5/2006 | Keogh et al. | |
| 2006/0110370 A1 | 5/2006 | Pathak et al. | |
| 2006/0159641 A1 | 7/2006 | Girardot et al. | |
| 2006/0193885 A1 | 8/2006 | Leonard Neethling et al. | |
| 2006/0210960 A1 | 9/2006 | Livesey et al. | |
| 2006/0217804 A1 | 9/2006 | Dove | |
| 2006/0217805 A1 | 9/2006 | Dove | |
| 2007/0050014 A1 | 3/2007 | Johnson | |
| 2007/0073392 A1 | 3/2007 | Heyninck-Jantz et al. | |
| 2007/0203576 A1 | 8/2007 | Lee et al. | |
| 2007/0254005 A1 | 11/2007 | Pathak et al. | |
| 2008/0302372 A1 | 12/2008 | Davidson et al. | |
| 2008/0319166 A1 | 12/2008 | Shen | |
| 2009/0041729 A1 | 2/2009 | Wolfinbarger, Jr. et al. | |
| 2009/0130162 A2 | 5/2009 | Pathak et al. | |
| 2009/0137999 A1 | 5/2009 | Silberberg et al. | |
| 2009/0188900 A1 | 7/2009 | Cali et al. | |
| 2009/0254175 A1 * | 10/2009 | Quijano | A61F 2/2418 623/1.24 |
| 2009/0326524 A1 | 12/2009 | Cali et al. | |
| 2010/0036484 A1 | 2/2010 | Hariton et al. | |
| 2011/0092966 A1 | 4/2011 | Guo et al. | |
| 2011/0177150 A1 | 7/2011 | Pathak et al. | |
| 2011/0214398 A1 | 9/2011 | Liburd et al. | |
| 2011/0238167 A1 | 9/2011 | Dove et al. | |
| 2011/0295363 A1 | 12/2011 | Girard et al. | |
| 2011/0300625 A1 | 12/2011 | Paniagua et al. | |
| 2011/0306124 A1 | 12/2011 | Strasly et al. | |
| 2011/0311493 A1 | 12/2011 | Dove et al. | |
| 2011/0319991 A1 * | 12/2011 | Hariton | B05B 1/185 623/2.14 |
| 2012/0035720 A1 | 2/2012 | Cali et al. | |
| 2012/0059487 A1 | 3/2012 | Cunanan et al. | |
| 2012/0067855 A1 | 3/2012 | Guo et al. | |
| 2012/0078356 A1 | 3/2012 | Fish et al. | |
| 2012/0095551 A1 | 4/2012 | Navia et al. | |
| 2012/0101572 A1 * | 4/2012 | Kovalsky | A61F 2/2418 623/2.19 |
| 2012/0123557 A1 | 5/2012 | Carpentier et al. | |
| 2012/0185038 A1 | 7/2012 | Fish et al. | |
| 2012/0328905 A1 | 12/2012 | Guo et al. | |
| 2013/0122583 A1 | 5/2013 | Neethling | |
| 2013/0150957 A1 * | 6/2013 | Weber | A61F 2/2412 623/2.15 |
| 2013/0238088 A1 | 9/2013 | Navia et al. | |
| 2014/0249623 A1 | 9/2014 | Matheny | |
| 2014/0330370 A1 | 11/2014 | Matheny et al. | |
| 2015/0088247 A1 | 3/2015 | L'Heureux et al. | |
| 2015/0094802 A1 * | 4/2015 | Buchbinder | A61F 2/2454 623/2.38 |
| 2016/0175095 A1 | 6/2016 | Dienno et al. | |
| 2017/0056164 A1 * | 3/2017 | Wang | A61F 2/2415 |
| 2017/0173214 A1 * | 6/2017 | Wang | A61L 27/3687 |
| 2018/0228602 A1 * | 8/2018 | Weber | A61F 31/10 |
| 2018/0325664 A1 * | 11/2018 | Gonda | A61F 2/2409 |
| 2019/0224369 A1 * | 7/2019 | Rzany | A61L 27/56 |
| 2020/0060814 A1 * | 2/2020 | Murphy | A61F 2/2475 |
| 2020/0323629 A1 * | 10/2020 | Girard | A61F 2/2412 |
| 2020/0330223 A1 * | 10/2020 | Howard | A61F 2/2418 |
| 2021/0060208 A1 * | 3/2021 | Hoerstrup | A61L 27/18 |
| 2021/0267755 A1 * | 9/2021 | Wallace | A61F 2/2409 |
| 2022/0023034 A1 * | 1/2022 | van der Burgt | D01D 5/0084 |
| 2022/0047385 A1 * | 2/2022 | Gray | A61L 31/148 |

FOREIGN PATENT DOCUMENTS

| | | |
|---|---|---|
| WO | 9613227 A1 | 5/1996 |
| WO | 9807452 A1 | 2/1998 |
| WO | 9843556 A1 | 10/1998 |
| WO | 0032252 A1 | 6/2000 |
| WO | 2004082536 A1 | 9/2004 |
| WO | 2006026325 A2 | 3/2006 |
| WO | 2006099334 A2 | 9/2006 |
| WO | 2013009851 A2 | 1/2013 |

OTHER PUBLICATIONS

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as Aa Ligament Substitute," Journal of Bio-

(56) References Cited

OTHER PUBLICATIONS medical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Grabenwoger, M. et al. "Decreased Tissue Reaction to Bioprosthetic Heart Valve Material after L-glutaimc acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium-Binding Amino Acid, y-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, issue 5, 1996, pp. 471-484.

Khor, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An independent Determinant of Early Bioprosthetic Calcification in Humans," Ann. Throac. Surg 2008;86:491-495.

Neethling, W., et al., "Enhanced Biostability and Biocompatibility of Decellularized Bovine Pericardium, Crosslinked with an Ultra-Low Concentration Monomeric Aldehyde and Treated with ADAPT®," J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003;12(1):93-100.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

\* cited by examiner

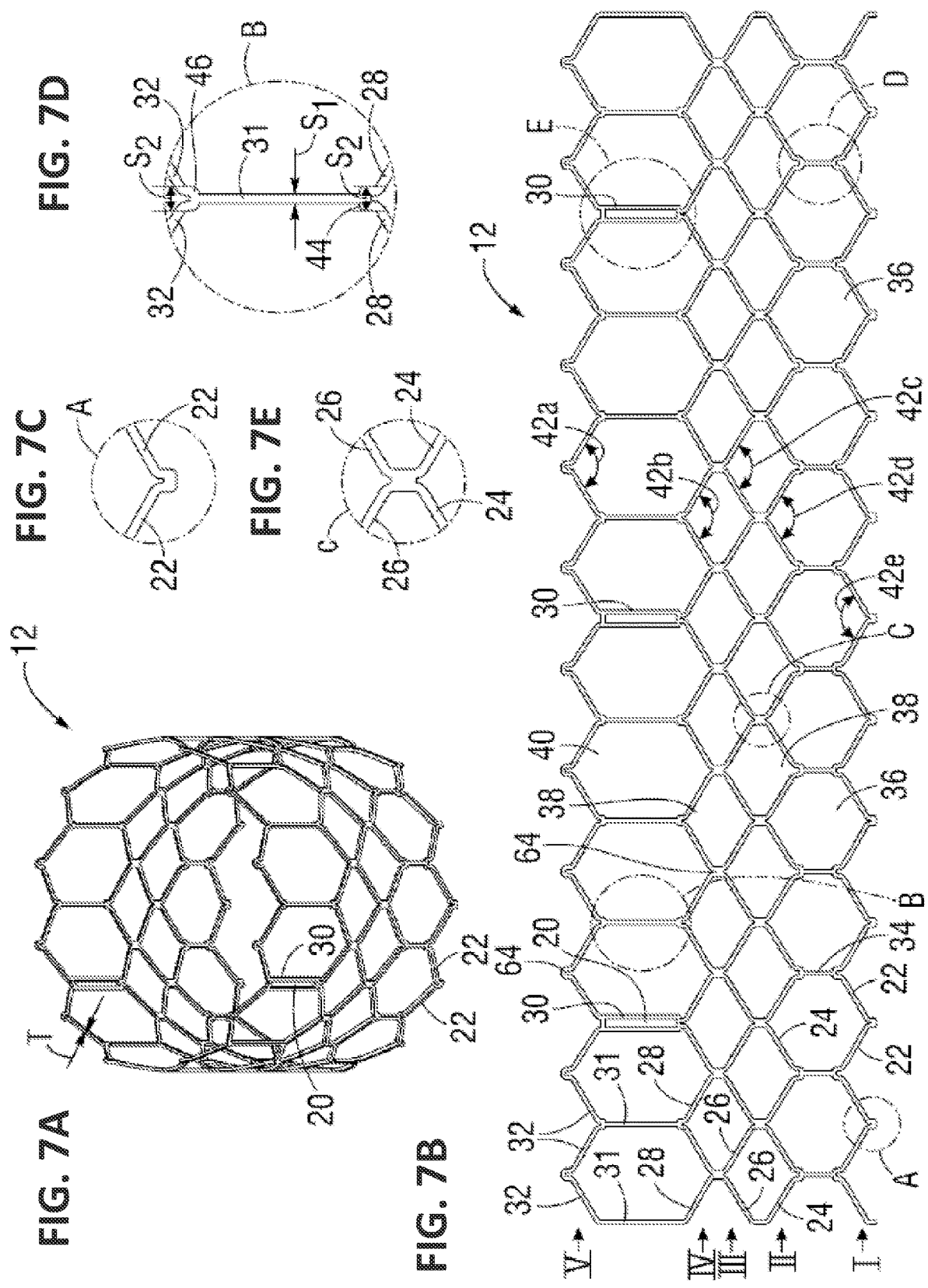

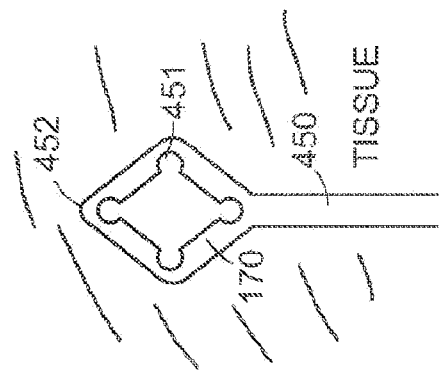
FIG. 8A
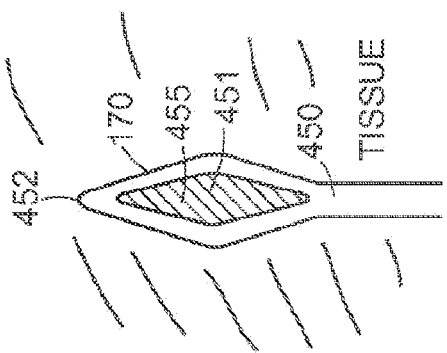
FIG. 8B
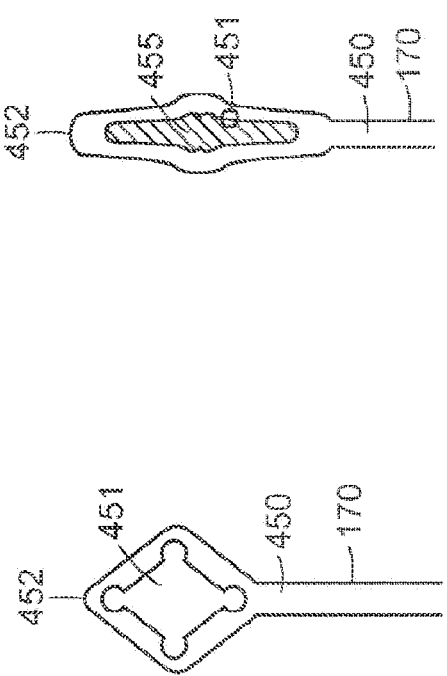
FIG. 8C
FIG. 8D
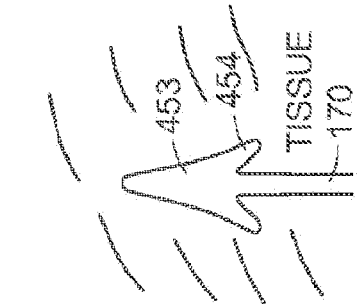
FIG. 8E
FIG. 8F
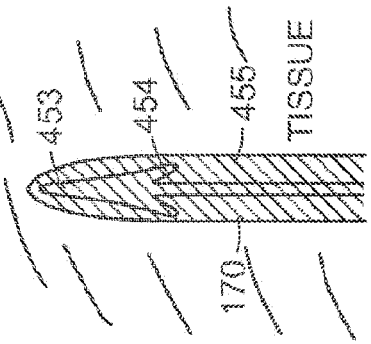
FIG. 8G
FIG. 8H

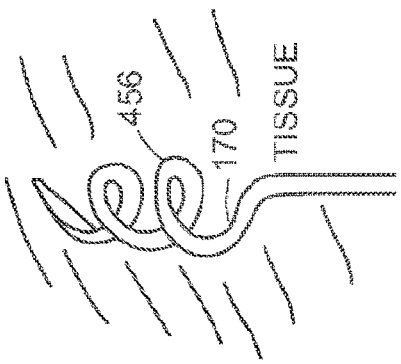
FIG. 8I
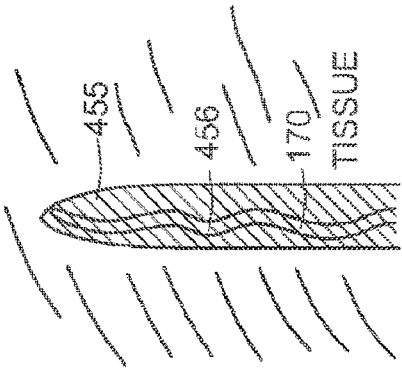
FIG. 8J
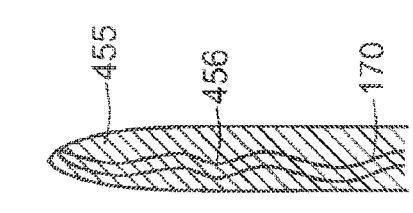
FIG. 8K
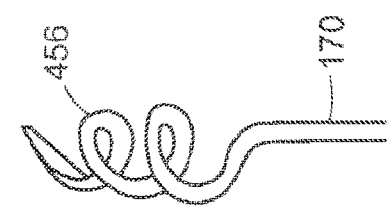
FIG. 8L
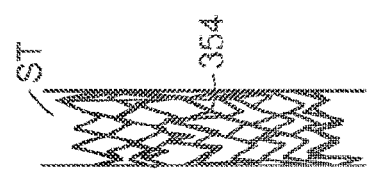
FIG. 8M
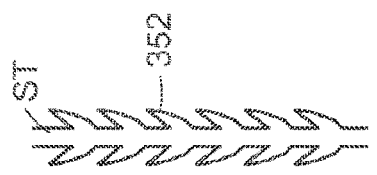
FIG. 8N  FIG. 8O  FIG. 8P
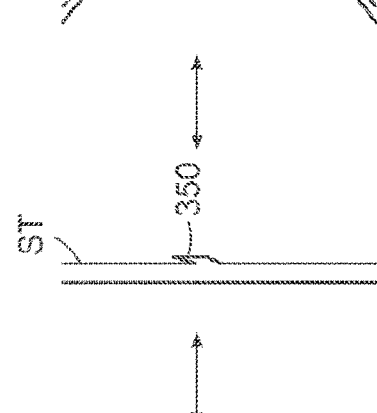
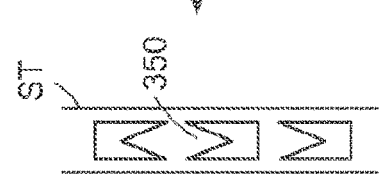
FIG. 8Q
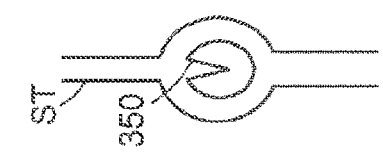
FIG. 8R

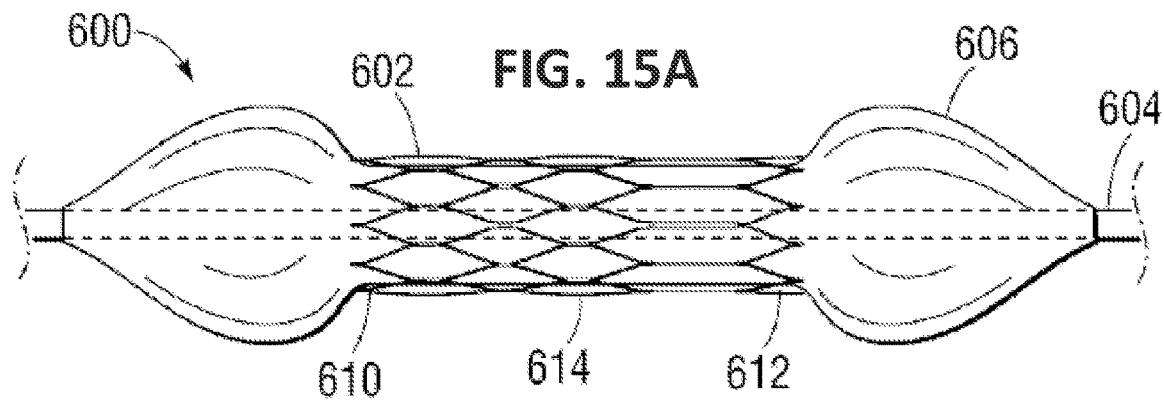
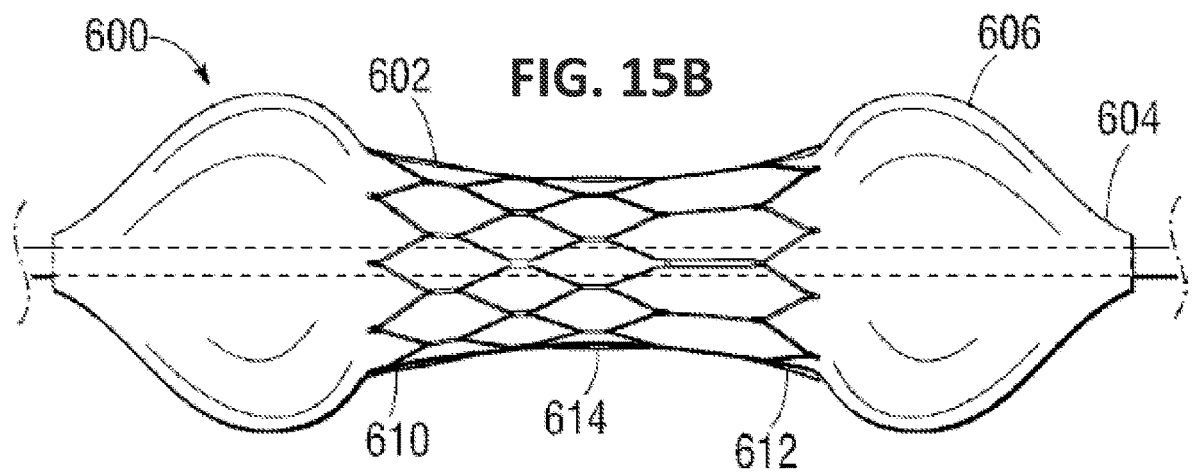
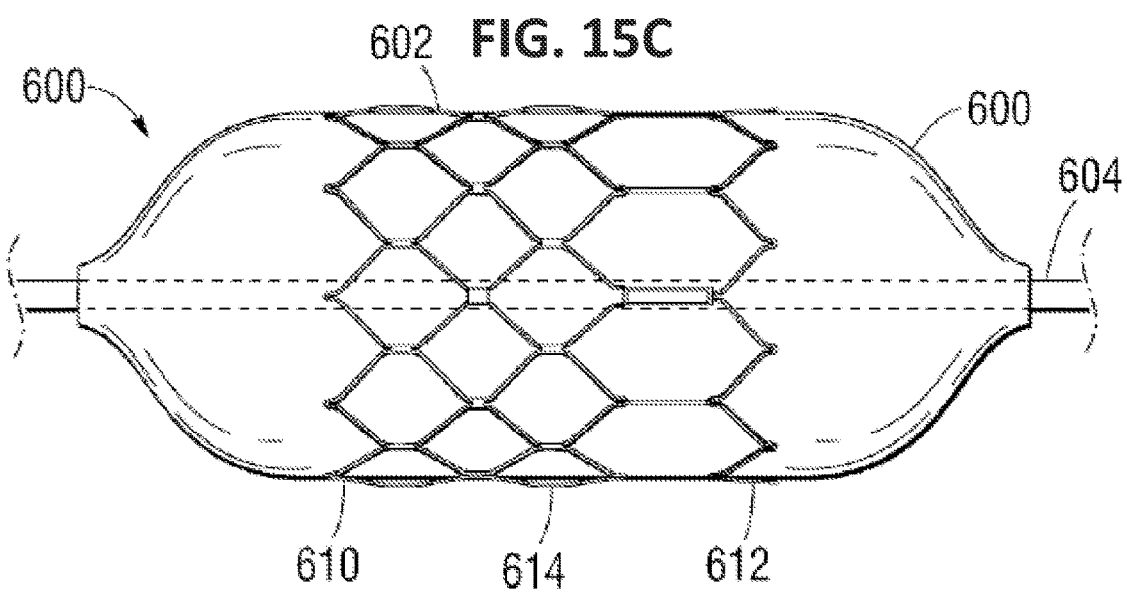

TRANSCATHETER PULMONIC REGENERATIVE VALVE

CROSS REFERENCE TO RELATED APPLICATIONS

This application claims the benefit of U.S. Application No. 62/754,102, filed Nov. 1, 2018, the content of which is incorporated by reference in its entirety into the present disclosure for all purposes.

TECHNICAL FIELD

The present disclosure is directed to artificial pulmonic valves and applications thereof, more particularly, pulmonic valves constructed of a bioabsorbable frame and regenerative tissue that can integrate with living tissue of a recipient of the artificial valve.

BACKGROUND

The human heart can suffer from various valvular diseases. These valvular diseases can result in significant malfunctioning of the heart and ultimately require replacement of the native valve with an artificial valve. Additionally, valvular diseases can affect children and adolescents, who are young and still growing and developing. When children or adolescents receive replacement valves, the artificial valves do not grow along with the recipient, as such, the artificial valves must be replaced in children to compensate for the growing heart. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Additionally, current artificial valves are static in size and do not grow or adjust to growing bodies. As such, children and adolescents suffering from valvular diseases require multiple procedures to replace artificial valves with larger valves to compensate for the recipient's growth. Since multiple procedures are required as children and adolescents grow, risks and dangers inherent to replacement processes increase with these individuals.

Further, because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference in their entireties, describe collapsible transcatheter heart valves that can be percutaneously introduced in a compressed state on a catheter and expanded in the desired position by balloon inflation or by utilization of a self-expanding frame or stent.

SUMMARY

Artificial heart valves and methods of use in accordance with embodiments of the invention are disclosed. In one embodiment, an implantable artificial heart valve includes a frame having a longitudinal axis extending between an inflow end of the frame and an outflow end of the frame, the inflow end of the frame being configured to receive antegrade blood flowing into the prosthetic valve when implanted, a leaflet structure positioned within the frame and constructed of a regenerative tissue, and an inner skirt positioned around an inner surface of the frame and extending along the longitudinal axis, the inner skirt is constructed of a second regenerative tissue.

In a further embodiment, the frame is constructed of a bioabsorb able material.

In another embodiment, the bioabsorbable material is selected from the group of poly(L-lactide), poly(L-lactide), polyglycolide, poly(L-lactide-co-glycolide), polyhydroxyalkanoate, polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate, polyhydroxyvalerate, poly-orthoesters, poly-anhydrides, polyiminocarbonate, and copolymers and combinations thereof.

In a still further embodiment, the leaflet structure and inner skirt are constructed of the same regenerative tissue.

In still another embodiment, the frame also including a plurality of commissure window frames to allow attachment of the leaflet structure.

In a yet further embodiment, the commissure window frames are constructed of a non-bioabsorbable material, and the frame is constructed of a bioabsorbable material.

In yet another embodiment, the leaflet structure including a plurality of leaflets, each leaflet includes a body portion having a free outflow edge, two opposing upper tabs extending from opposite sides of the body portion, and two opposing lower tabs, each lower tab extending from the body portion adjacent to a respective upper tab, the lower tabs extending from the body portion at opposite ends of the free outflow edge.

In a further embodiment again, the lower tabs are folded about radially extending creases that extend radially from the opposite ends of the free outflow edge, such that a first portion of the lower tabs lies flat against the body portion of the respective leaflet, and the lower tabs are folded about axially extending creases such that a second portion of the lower tabs extends in a different plane than the first portion, the radially extending creases and the axially extending creases are non-parallel.

In another embodiment again, the second portion of each lower tab is sutured to a respective upper tab.

In a further additional embodiment, the frame is radially collapsible to a collapsed configuration and radially expandable to an expanded configuration.

In another additional embodiment, the frame also includes tissue engaging elements to allow fixation of the artificial heart valve to the wall of a blood vessel.

In a still yet further embodiment, the tissue engaging elements include a bioabsorbable glue to prevent the tissue engaging elements from expanding and allowing the artificial heart valve to be repositioned.

In still yet another embodiment, the regenerative tissue and second regenerative tissue are selected from the group of polyglactin, collagen, and polyglycolic acid.

In a still further embodiment again, the regenerative tissue also includes extracellular matrix proteins selected from the group of hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof.

In still another embodiment again, the inner skirt extends beyond at least one of the outflow end and inflow end of the frame and forms an outer skirt attached to an outer surface of the frame.

In a still further additional embodiment, the frame also includes growth factors to promote integration of the regenerative tissue.

In yet another embodiment, an outer diameter of the inflow end portion of the frame is smaller than an outer diameter of the outflow end portion of the frame.

In a further still embodiment again, the frame has a plurality of openings and portions of the leaflet structure protrude through the openings while the prosthetic valve is in a radially collapsed configuration.

In still another additional embodiment, an assembly for implanting an artificial heart valve in a patient's body includes a delivery apparatus includes an elongated shaft and a radially expandable artificial heart valve adapted to be mounted on the shaft in a radially collapsed configuration for delivery into the body, the prosthetic heart valve including a frame having an inflow end portion defining an inflow end of the frame that is configured to receive antegrade blood flow into the artificial heart valve when implanted, and the frame also having an outflow end portion defining an outflow end of the frame opposite the inflow end of the frame, the prosthetic heart valve also includes a leaflet structure positioned within the frame, an inner skirt positioned along an inner surface of the frame, the leaflet structure is constructed of a regenerative tissue, and the inner skirt is constructed of a second regenerative tissue.

In a yet further embodiment again, the frame is constructed of a bioabsorbable material.

In another embodiment, the bioabsorbable material is selected from the group of poly(L-lactide), poly(L-lactide), polyglycolide, poly(L-lactide-co-glycolide), polyhydroxyalkanoate, polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate, polyhydroxyvalerate, poly-orthoesters, poly-anhydrides, polyiminocarbonate, and copolymers and combinations thereof.

In a still further embodiment, the leaflet structure and inner skirt are constructed of the same regenerative tissue.

In yet another embodiment again, the frame also includes a plurality of commissure window frames to allow attachment of the leaflet structure.

In a yet further additional embodiment, the commissure window frames are constructed of a non-bioabsorbable material, and the frame is constructed of a bioabsorbable material.

In yet another additional embodiment, an outer diameter of the inflow end portion of the frame is smaller than an outer diameter of the outflow end portion of the frame.

In a further additional embodiment again, the frame has a plurality of openings and portions of the leaflet structure protrude through the openings while the prosthetic valve is in the radially collapsed configuration.

In another additional embodiment again, the leaflet structure includes a plurality of leaflets, each leaflet including a body portion having a free outflow edge, two opposing upper tabs extending from opposite sides of the body portion, and two opposing lower tabs, each lower tab extending from the body portion adjacent to a respective upper tab, the lower tabs extending from the body portion at opposite ends of the free outflow edge.

In a further embodiment again, the lower tabs are folded about radially extending creases that extend radially from the opposite ends of the free outflow edge, such that a first portion of the lower tabs lies flat against the body portion of the respective leaflet, and the lower tabs are folded about axially extending creases such that a second portion of the lower tabs extends in a different plane than the first portion, the radially extending creases and the axially extending creases are non-parallel.

In another embodiment again, the second portion of each lower tab is sutured to a respective upper tab.

In a still yet further embodiment again, the inner skirt extends beyond at least one of the outflow end and inflow end of the frame and forms an outer skirt attached to an outer surface of the frame.

In still yet another embodiment again, the frame also includes tissue engaging elements to allow fixation of the artificial heart valve to the wall of a blood vessel.

In a still yet further embodiment, the tissue engaging elements include a bioabsorbable glue to prevent the tissue engaging elements from expanding and allowing the artificial heart valve to be repositioned.

In a still yet further additional embodiment, the delivery apparatus also includes an inflatable balloon surrounding a portion of the elongated shaft, the radially expandable artificial heart valve is positioned over the balloon.

In still yet another additional embodiment, the delivery apparatus also includes an outer sleeve, the radially expandable artificial heart valve is disposed in the outer sleeve.

In still yet another embodiment, the regenerative tissue and second regenerative tissue are selected from the group of polyglactin, collagen, and polyglycolic acid.

In a still further embodiment again, the regenerative tissue also includes extracellular matrix proteins selected from the group of hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof.

In still another embodiment again, the inner skirt extends beyond at least one of the outflow end and inflow end of the frame and forms an outer skirt attached to an outer surface of the frame.

In a still further additional embodiment, the frame also includes growth factors to promote integration of the regenerative tissue.

A further embodiment includes a method of implanting an artificial heart valve using a catheter including accessing the vascular system of a patient, advancing a radially expandable artificial heart valve to the pulmonary artery of the patient, where the artificial heart valve is in a radially collapsed configuration and including a frame having an inflow end portion defining an inflow end of the frame that is configured to receive antegrade blood flow into the artificial heart valve when implanted, and the frame also having an outflow end portion defining an outflow end of the frame opposite the inflow end of the frame, the prosthetic heart valve also including a leaflet structure positioned within the frame, an inner skirt positioned along an inner surface of the frame, the leaflet structure is constructed of a regenerative tissue, and the inner skirt is constructed of a second regenerative tissue, and the artificial heart valve is mounted on a delivery apparatus, and delivering the radially expandable artificial heart valve to the pulmonary artery of the patient.

In a yet further additional embodiment again, access to the vascular system of a patient is accomplished percutaneously.

In yet another additional embodiment again, access to the vascular system of a patient is accomplished by accessing the femoral vein.

In a still yet further additional embodiment again, the advancing step is performed by way of the femoral vein, inferior vena cava, tricuspid valve, and right ventricle of the patient.

In still yet another additional embodiment again, the delivery apparatus is a catheter.

In another further embodiment, the catheter is a balloon catheter including a balloon, the balloon is deflated, the radially expandable artificial heart valve is positioned over the balloon, and the delivering step is accomplished by inflating the balloon, the inflating balloon radially expands the radially expandable artificial heart valve.

In still another further embodiment, the catheter is a sheath catheter including an outer sleeve, the radially expandable artificial heart valve is disposed in the outer sleeve, the delivering step is accomplished by retracting the outer sleeve, and the retracting sleeve allows the radially expandable artificial heart valve to expand.

In yet another further embodiment, the frame is constructed of a bioabsorb able material.

In another embodiment, the bioabsorbable material is selected from the group of poly(L-lactide), poly(L-lactide), polyglycolide, poly(L-lactide-co-glycolide), polyhydroxyalkanoate, polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate, polyhydroxyvalerate, poly-orthoesters, poly-anhydrides, polyiminocarbonate, and copolymers and combinations thereof.

In another further embodiment again, the frame also includes a plurality of commissure window frames to allow attachment of the leaflet structure.

Another further additional embodiment, the commissure window frames are constructed of a non-bioabsorbable material, and the frame is constructed of a bioabsorbable material.

In a still further embodiment, the leaflet structure and inner skirt are constructed of the same regenerative tissue.

In another additional embodiment again, the leaflet structure includes a plurality of leaflets, each leaflet including a body portion having a free outflow edge, two opposing upper tabs extending from opposite sides of the body portion, and two opposing lower tabs, each lower tab extending from the body portion adjacent to a respective upper tab, the lower tabs extending from the body portion at opposite ends of the free outflow edge.

In a further embodiment again, the lower tabs are folded about radially extending creases that extend radially from the opposite ends of the free outflow edge, such that a first portion of the lower tabs lies flat against the body portion of the respective leaflet, and the lower tabs are folded about axially extending creases such that a second portion of the lower tabs extends in a different plane than the first portion, the radially extending creases and the axially extending creases are non-parallel.

In another embodiment again, the second portion of each lower tab is sutured to a respective upper tab.

In still yet another embodiment again, the frame also includes tissue engaging elements to allow fixation of the artificial heart valve to the wall of a blood vessel.

In a still yet further embodiment, the tissue engaging elements include a bioabsorbable glue to prevent the tissue engaging elements from expanding and allowing the artificial heart valve to be repositioned.

In still yet another embodiment, the regenerative tissue and second regenerative tissue are selected from the group of polyglactin, collagen, and polyglycolic acid.

In a still further embodiment again, the regenerative tissue also includes extracellular matrix proteins selected from the group of hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof.

In still another embodiment again, the inner skirt extends beyond at least one of the outflow end and inflow end of the frame and forms an outer skirt attached to an outer surface of the frame.

In a still further additional embodiment, the frame also includes growth factors to promote integration of the regenerative tissue.

In yet another additional embodiment, an outer diameter of the inflow end portion of the frame is smaller than an outer diameter of the outflow end portion of the frame.

In a further additional embodiment again, the frame has a plurality of openings and portions of the leaflet structure protrude through the openings while the prosthetic valve is in the radially collapsed configuration.

A yet further embodiment includes a method of treating a patient for a valvular disease including identifying a valvular disease in a patient, implanting an artificial heart valve into a blood vessel of the patient, where the artificial heart valve including a frame having an inflow end portion defining an inflow end of the frame that is configured to receive antegrade blood flow into the artificial heart valve when implanted, and the frame also having an outflow end portion defining an outflow end of the frame opposite the inflow end of the frame, the prosthetic heart valve also including a leaflet structure positioned within the frame, an inner skirt positioned along an inner surface of the frame, the leaflet structure is constructed of a regenerative tissue, and the inner skirt is constructed of a second regenerative tissue.

In yet another further additional embodiment, the valvular disease is selected from the group of Tetralogy of Fallot and Transposition of the Great Arteries.

In another further additional embodiment, the implanting step is performed by open heart surgery.

In another further additional embodiment again, the open heart surgery involves a longitudinal incision along the pulmonary artery, up to and along one of the pulmonary branches.

In yet another further additional embodiment, the implanting step is performed by transcatheter insertion using a catheter including an elongated shaft, the artificial heart valve is radially expandable and in a radially collapsed configuration, and the artificial heart valve is mounted on the shaft.

In a further embodiment again, the transcatheter insertion is performed by percutaneously accessing a vascular system of the patient.

In a still further embodiment, the transcatheter insertion is performed by accessing a femoral vein of the patient.

In a still further additional embodiment, the catheter is advanced through the femoral vein, inferior vena cava, tricuspid valve, and right ventricle.

In still yet another embodiment again, the catheter is a balloon catheter including a balloon, where the balloon is deflated, the radially expandable artificial heart valve is positioned over the balloon, and where the delivering step is accomplished by inflating the balloon, where the inflating balloon radially expands the radially expandable artificial heart valve.

In a yet further additional embodiment again, the catheter is a sheath catheter including an outer sleeve, the radially expandable artificial heart valve is disposed in the outer sleeve, and the delivering step is accomplished by retracting the outer sleeve, the retracting outer sleeve allows the radially expandable artificial heart valve to expand.

In a still yet further additional embodiment, the frame is constructed of a bioabsorbable material.

In another embodiment, the bioabsorbable material is selected from the group of poly(L-lactide), poly(L-lactide), polyglycolide, poly(L-lactide-co-glycolide), polyhydroxyalkanoate, polysaccharides, proteins, polyesters, polyhydroxyalkanoates, polyalkelene esters, polyamides, poly-caprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate, polyhydroxyvalerate, poly-orthoesters, poly-anhydrides, polyiminocarbonate, and copolymers and combinations thereof.

In a yet further additional embodiment, the frame also includes a plurality of commissure window frames to allow attachment of the leaflet structure.

In another further embodiment again, the commissure window frames are constructed of a non-bioabsorbable material, and the frame is constructed of a bioabsorbable material.

In a still further embodiment, the leaflet structure and inner skirt are constructed of the same regenerative tissue.

In another additional embodiment again, the leaflet structure includes a plurality of leaflets, each leaflet including a body portion having a free outflow edge, two opposing upper tabs extending from opposite sides of the body portion, and two opposing lower tabs, each lower tab extending from the body portion adjacent to a respective upper tab, the lower tabs extending from the body portion at opposite ends of the free outflow edge.

In a further embodiment again, the lower tabs are folded about radially extending creases that extend radially from the opposite ends of the free outflow edge, such that a first portion of the lower tabs lies flat against the body portion of the respective leaflet, and the lower tabs are folded about axially extending creases such that a second portion of the lower tabs extends in a different plane than the first portion, the radially extending creases and the axially extending creases are non-parallel.

In another embodiment again, the second portion of each lower tab is sutured to a respective upper tab.

In still yet another embodiment again, the frame also includes tissue engaging elements to allow fixation of the artificial heart valve to the wall of a blood vessel.

In a still yet further embodiment, the tissue engaging elements include a bioabsorbable glue to prevent the tissue engaging elements from expanding and allowing the artificial heart valve to be repositioned.

In still yet another embodiment, the regenerative tissue and second regenerative tissue are selected from the group of polyglactin, collagen, and polyglycolic acid.

In a still further embodiment again, the regenerative tissue also includes extracellular matrix proteins selected from the group of hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof.

In still another embodiment again, the inner skirt extends beyond at least one of the outflow end and inflow end of the frame and forms an outer skirt attached to an outer surface of the frame.

In a still further additional embodiment, the frame also includes growth factors to promote integration of the regenerative tissue.

In yet another additional embodiment, an outer diameter of the inflow end portion of the frame is smaller than an outer diameter of the outflow end portion of the frame.

In a further additional embodiment again, the frame has a plurality of openings and portions of the leaflet structure protrude through the openings while the prosthetic valve is in the radially collapsed configuration.

Methods for treatment disclosed herein also encompass methods for simulating the treatment, for example, for training and education. Such methods can be performed on any suitable platform, for example, cadavers, portions thereof (e.g., cadaver hearts and/or vasculature), human or non-human; physical models; in silico; or in any combination of these platforms.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying drawings where:

FIGS. 7A-7G illustrate an exemplary frame of an artificial heart valve in accordance with certain embodiments of the invention.

FIGS. 8A-8R illustrate side views of exemplary tissue engaging elements in accordance with certain embodiments of the invention.

FIGS. 15A-15C illustrate deployment of an exemplary embodiment of an artificial heart valve using a balloon catheter in accordance with certain embodiments of the invention.

DETAILED DISCLOSURE OF THE INVENTION

Turning now to the diagrams and figures, embodiments of the invention are generally directed to artificial heart valves, and applications thereof. Although many embodiments are illustrated as being used within the pulmonary artery, other applications and other embodiments in addition to those described herein are within the scope of the technology, such that the artificial valves may be used in other areas of the anatomy, heart, or vasculature, such as the superior vena cava or the inferior vena cava. Additionally, embodiments of the technology may have different configurations, components, or procedures than those described herein. A person of ordinary skill in the art, therefore, will accordingly understand that the technology can have other embodiments with additional elements, or the technology can have other embodiments without several of the features shown and described below with illustrated in the figures herein.

It should be noted that various embodiments of artificial valves and systems for delivery and implant are disclosed herein, and any combination of these options may be made unless specifically excluded. Likewise, the different constructions of artificial valves may be mixed and matched, such as by combining any valve type and/or feature, tissue cover, etc., even if not explicitly disclosed. In short, individual components of the disclosed systems may be combined unless mutually exclusive or otherwise physically impossible.

For the sake of uniformity, in these Figures and others in the application the artificial valves are depicted such that the pulmonary bifurcation end is up, while the ventricular end is down. These directions may also be referred to as "distal" as a synonym for up or the pulmonary bifurcation end, and "proximal" as a synonym for down or the ventricular end, which are terms relative to the physician's perspective.

Figure 1A:
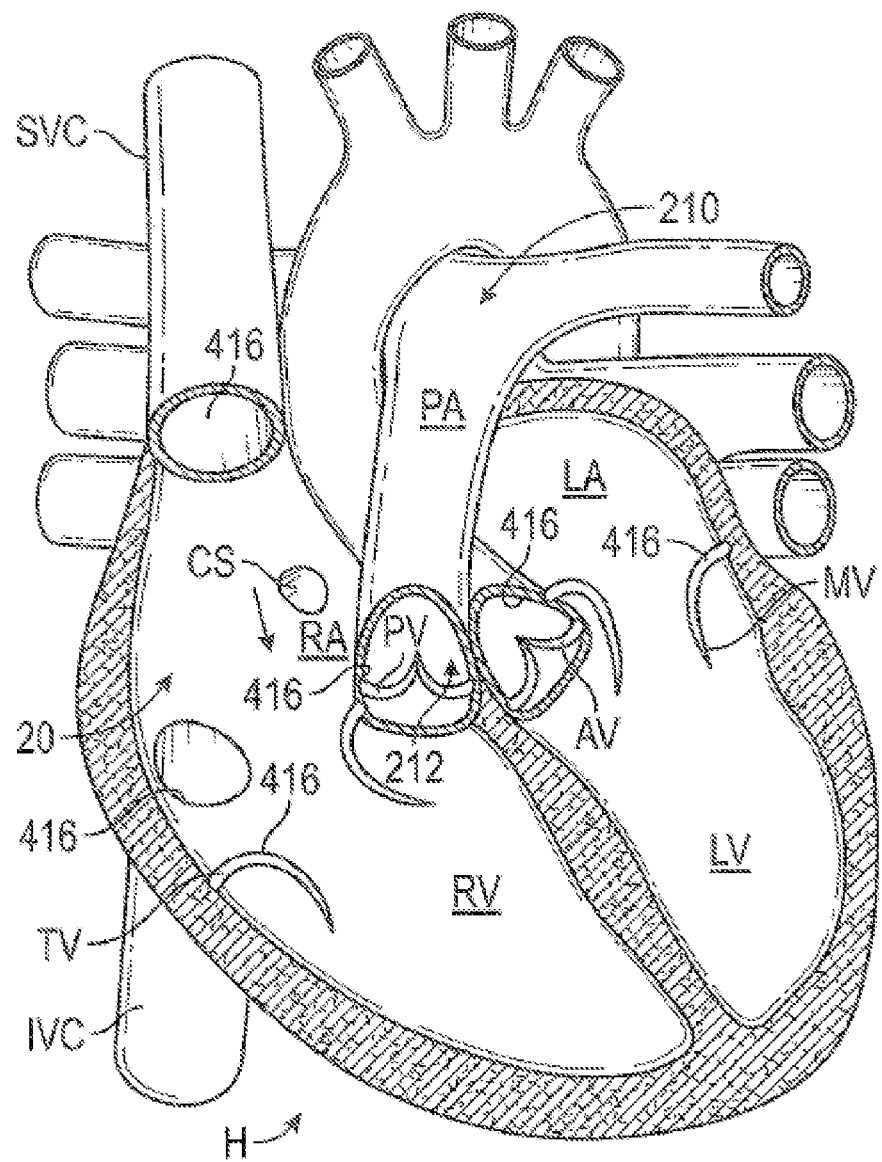
FIG. 1A illustrates a cutaway view of the human heart in a diastolic phase.
Figure 1B:
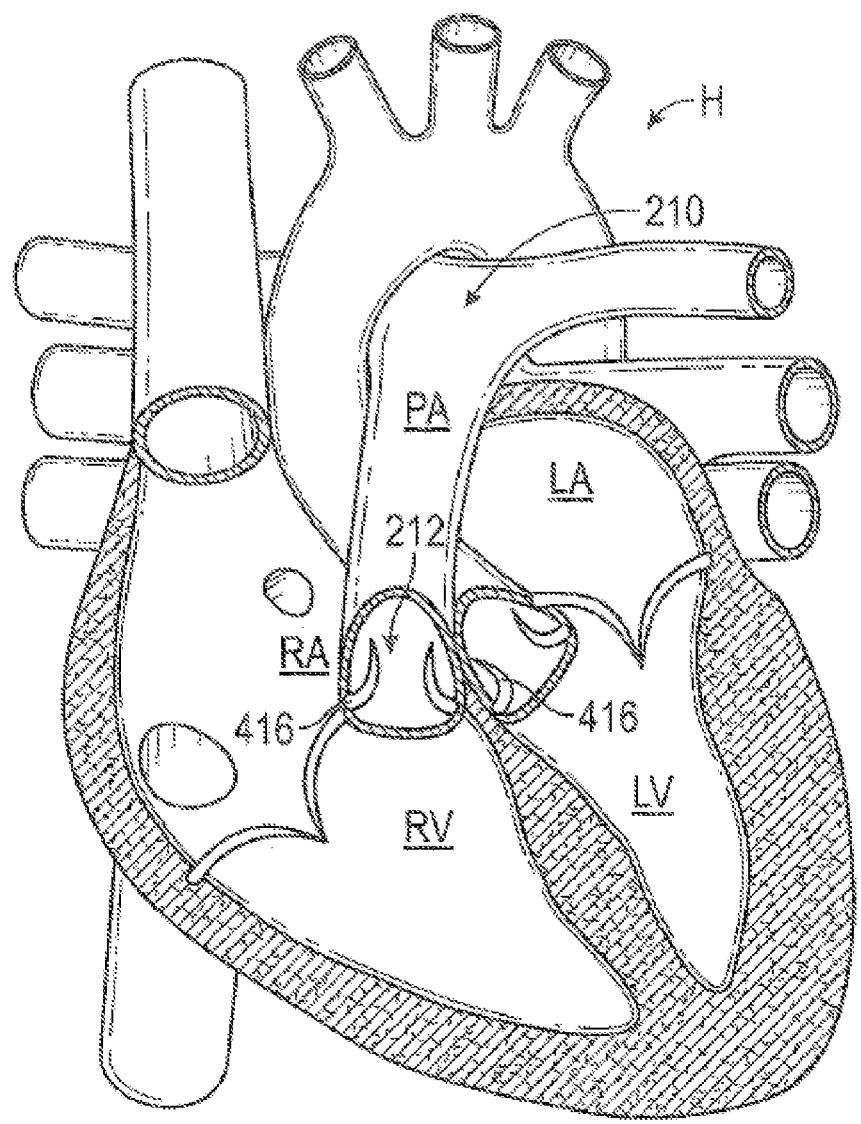
FIG. 1B illustrates a cutaway view of the human heart in a systolic phase.
Figure 2A:
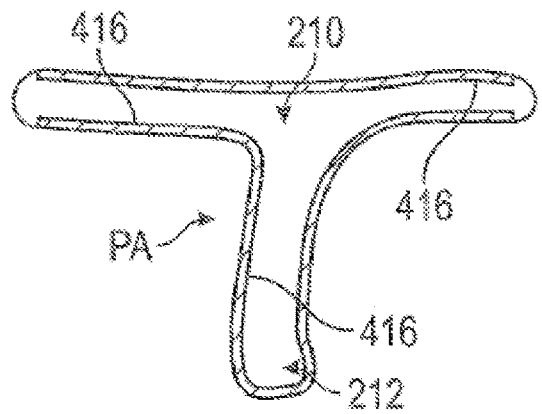
FIGS. 2A-2E illustrate sectional views of pulmonary arteries demonstrating that pulmonary arteries may have a variety of different shapes and sizes.
Figure 2B:
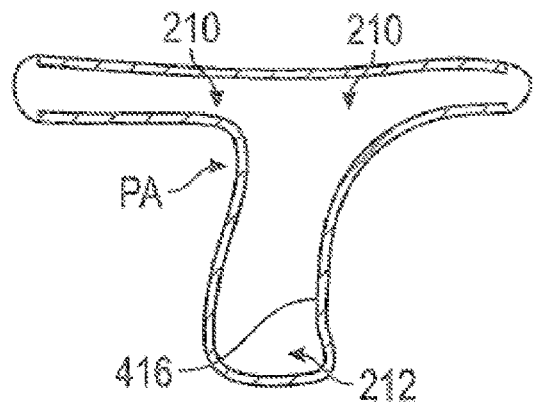
Figure 2C:
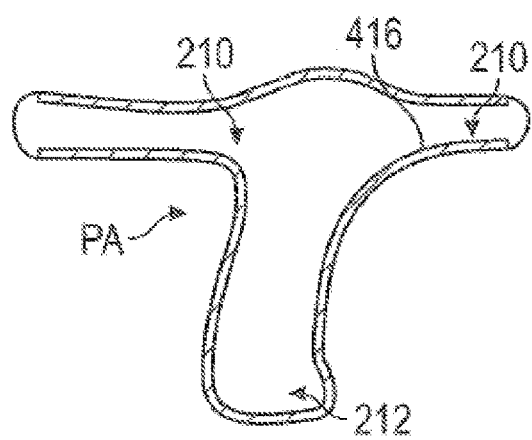
Figure 2D:
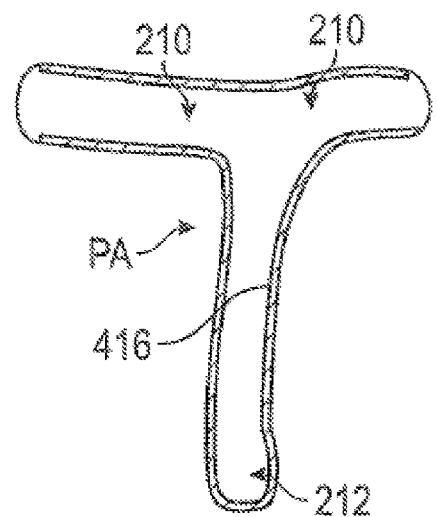
Figure 2E:
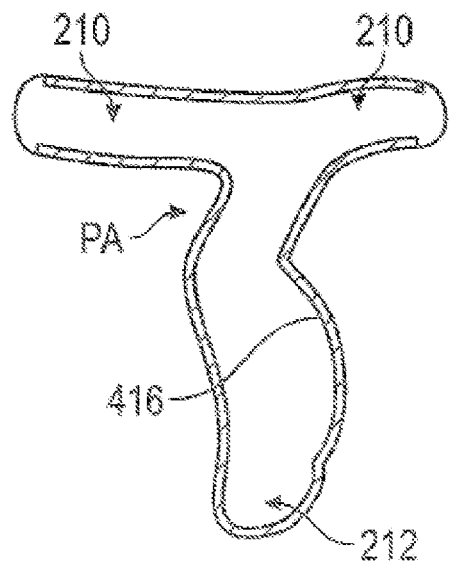
Figure 3A:
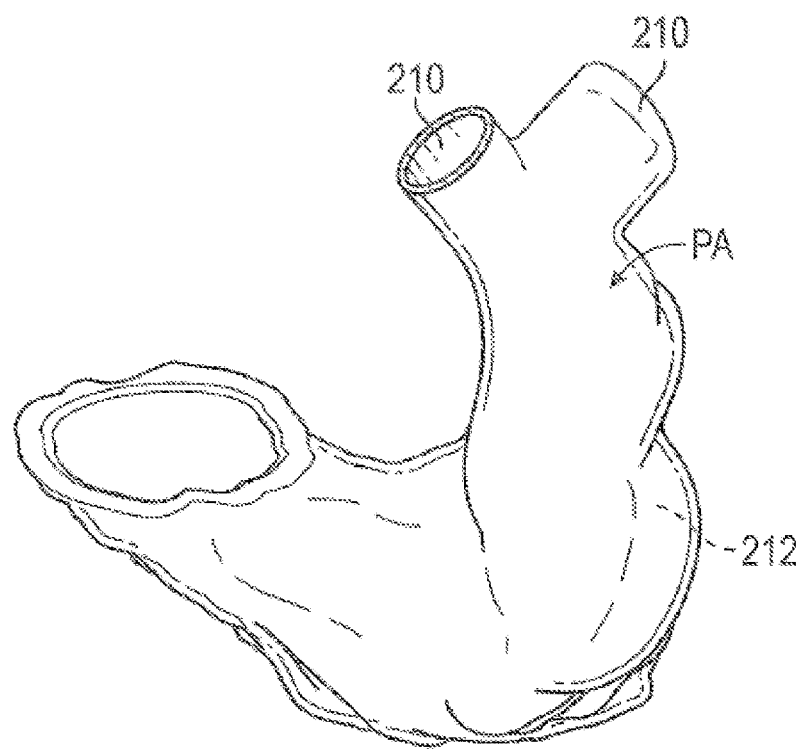
FIG. 3A-3D illustrate perspective views of pulmonary arteries demonstrating that pulmonary arteries may have a variety of different shapes and sizes.
Figure 3B:
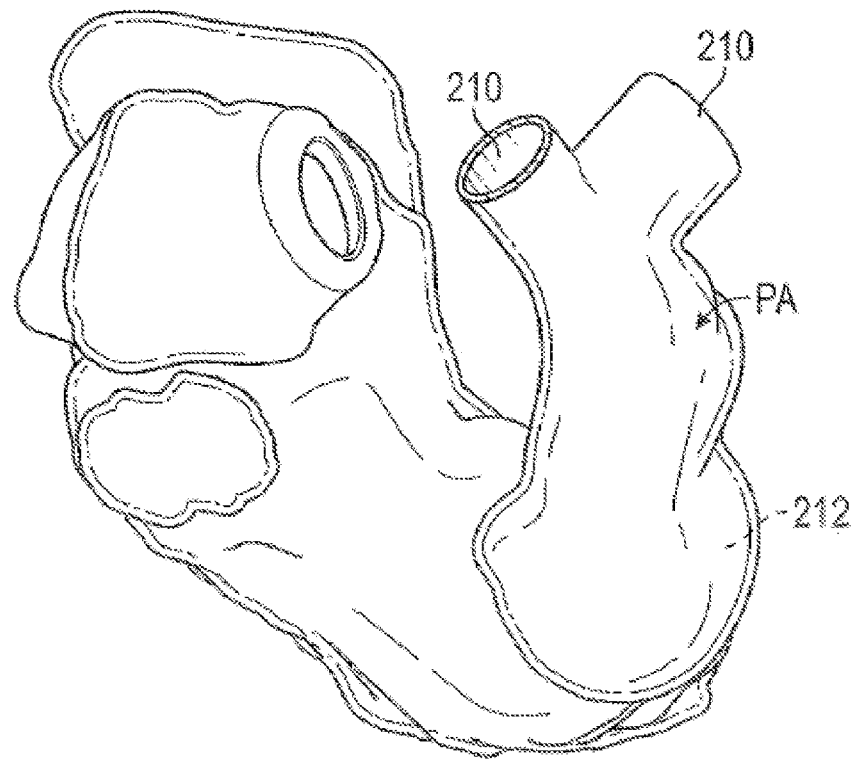
Figure 3C:
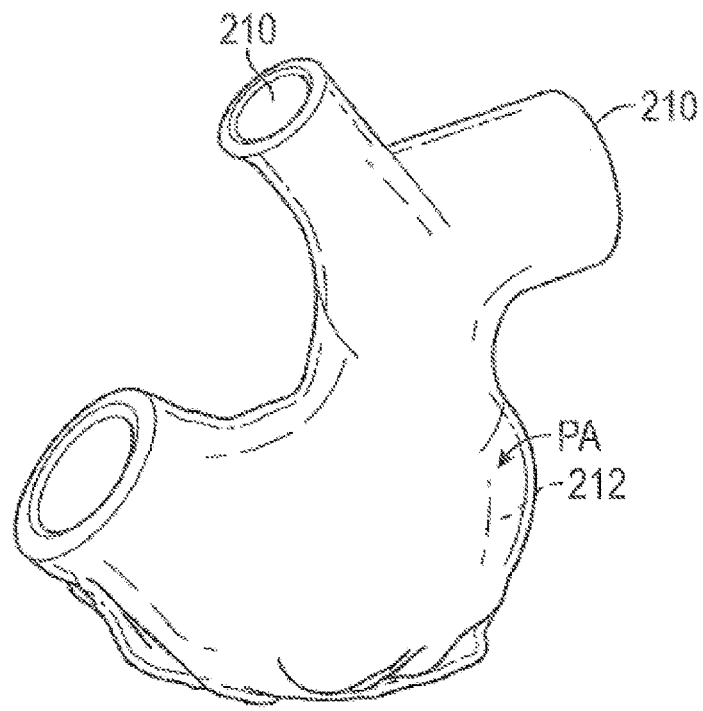
Figure 3D:
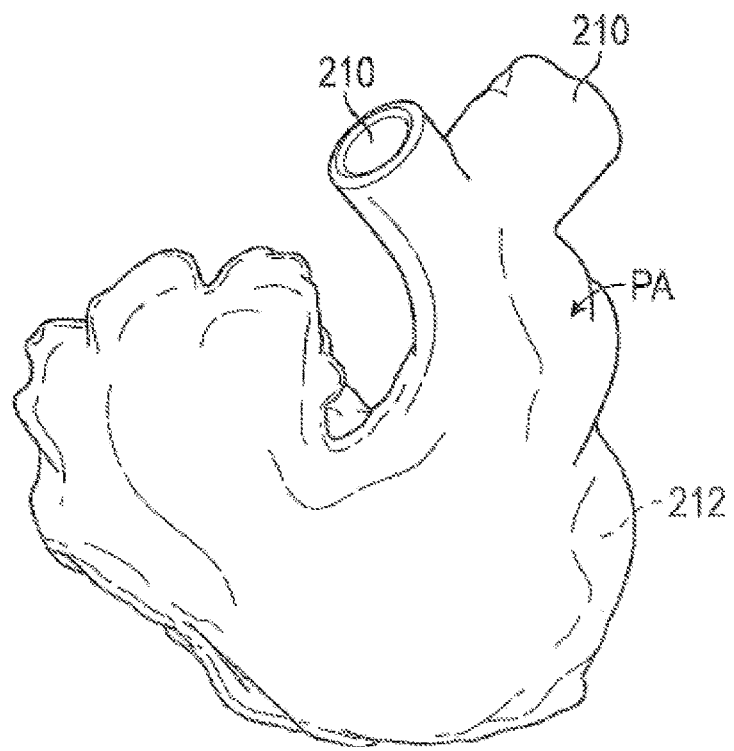

FIGS. 1A and 1B illustrate cutaway views of a human heart H in diastolic (FIG. 1A) and systolic (FIG. 1B) phases. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the main pulmonary artery PA. Each of these valves has flexible leaflets extending inward across the respective orifices that come together or "coapt" in the flowstream to form one-way, fluid-occluding surfaces. The artificial valves of the present application are described primarily with respect to the pulmonary valve. Therefore, anatomical structures of the right atrium RA and right ventricle RV will be explained in greater detail. It should be understood that the devices described herein may also be used in other areas, e.g., in the inferior vena cava and/or the superior vena cava as treatment for a regurgitant or otherwise defective tricuspid valve, in the aorta (e.g., an enlarged aorta) as treatment for a defective aortic valve, in other areas of the heart or vasculature, in grafts, etc.

The right atrium RA receives deoxygenated blood from the venous system through the superior vena cava SVC and the inferior vena cava IVC, the former entering the right atrium from above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA enters the tricuspid valve TV by expansion of the right ventricle RV. In the systolic phase, or systole, seen in FIG. 1B, the right ventricle RV contracts to force the venous blood through the pulmonary valve PV and pulmonary arteries into the lungs. In one exemplary embodiment, the devices described by the present application are used to replace or supplement the function of a defective pulmonary valve. During systole, the leaflets of the tricuspid valve TV close to prevent the venous blood from regurgitating back into the right atrium RA.

Referring to FIGS. 2A-2E and 3A-3D, the illustrated, non-exhaustive examples illustrate that the main pulmonary artery can have a wide variety of different shapes and sizes. For example, as shown in the sectional views of FIGS. 2A-2E and the perspective views of FIGS. 3A-3D, the length, diameter, and curvature or contour may vary greatly between main pulmonary arteries of different patients. Further, the diameter may vary significantly along the length of an individual main pulmonary artery. These differences can be even more significant in main pulmonary arteries that suffer from certain conditions and/or have been compromised by previous surgery. For example, the treatment of Tetralogy of Fallot (TOF) or Transposition of the Great Arteries (TGA) often results in larger and more irregularly shaped main pulmonary arteries.

Tetralogy of Fallot (TOF) is a cardiac anomaly that refers to a combination of four related heart defects that commonly occur together. The four defects are ventricular septal defect (VSD), overriding aorta (where the aortic valve is enlarged and appears to arise from both the left and right ventricles instead of the left ventricle as in normal hearts), pulmonary stenosis (a narrowing of the pulmonary valve and outflow tract or area below the valve that creates an obstruction of blood flow from the right ventricle to the main pulmonary artery), and right ventricular hypertrophy (thickening of the muscular walls of the right ventricle, which occurs because the right ventricle is pumping at high pressure).

Transposition of the Great Arteries (TGA) refers to an anomaly where the aorta and the pulmonary artery are "transposed" from their normal position so that the aorta arises from the right ventricle and the pulmonary artery from the left ventricle.

Surgical treatment for some conditions involves a longitudinal incision along the pulmonary artery, up to and along one of the pulmonary branches. This incision can eliminate or significantly impair the function of the pulmonary valve. A trans-annular patch is used to cover the incision after the surgery. The trans-annular patch can reduce stenotic or constrained conditions of the main pulmonary artery PA, associated with other surgeries. However, the trans-annular patch technique can also result in main pulmonary arteries having a wide degree of variation in size and shape (See FIGS. 3A-3D). The impairment or elimination of the pulmonary valve PV can create significant regurgitation and, prior to the present invention, often required later open heart surgery to replace the pulmonary valve.

Figure 4A:
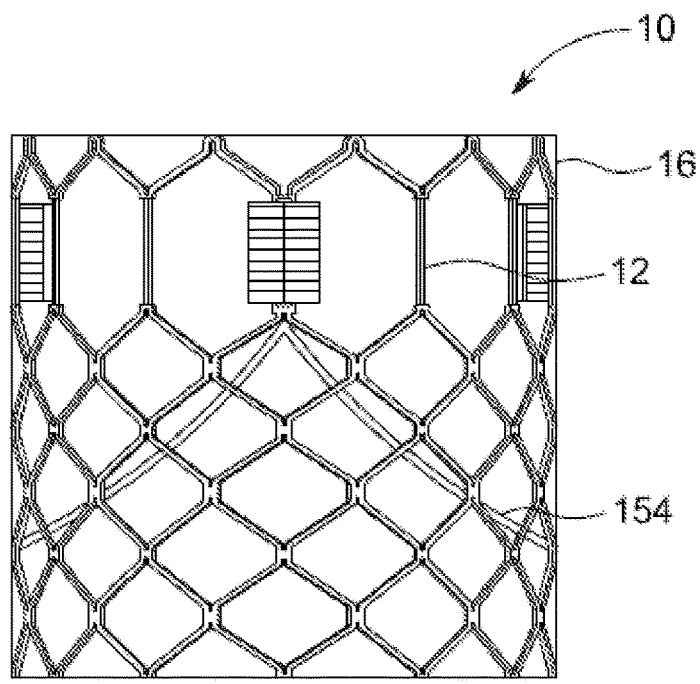
FIG. 4A illustrates a side view an exemplary artificial valve in accordance with certain embodiments of the invention.
Figure 4B:
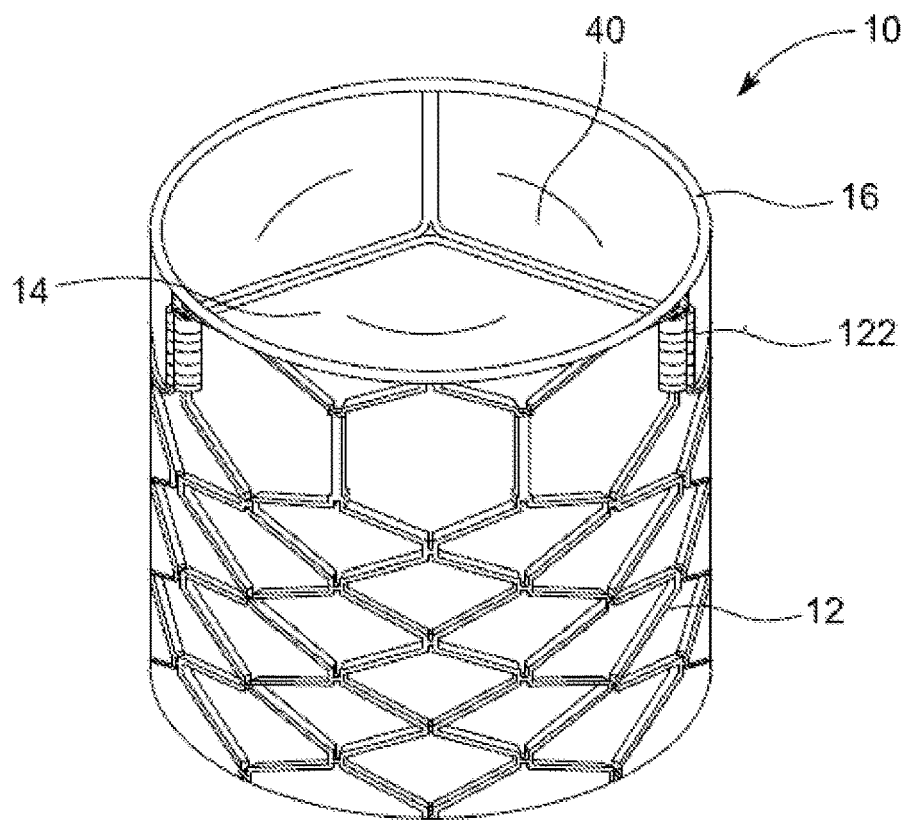
FIG. 4B illustrates a perspective view of an exemplary artificial valve in accordance with certain embodiments of the invention.
Figure 4C:
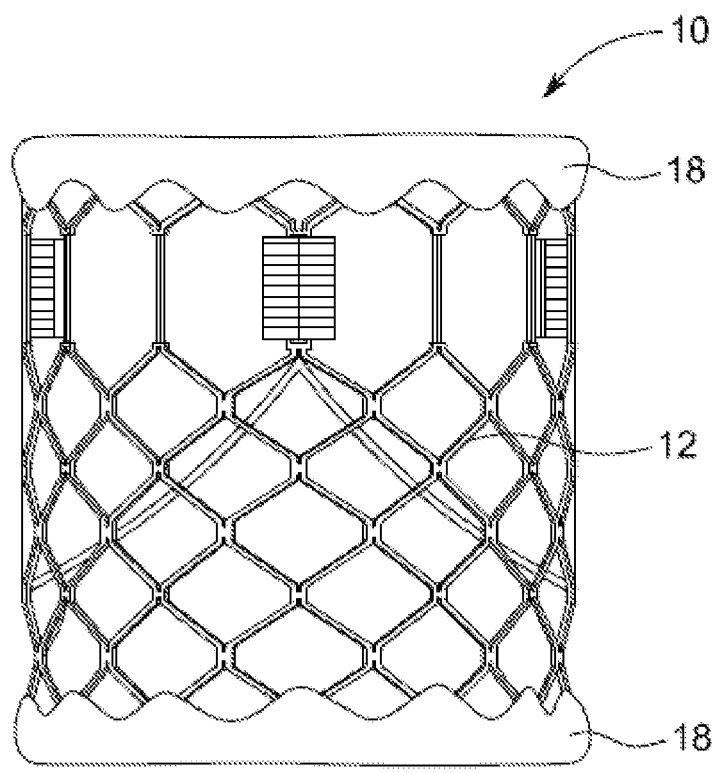
FIG. 4C-4D illustrate side views of exemplary artificial valves in accordance with certain embodiments of the invention.
Figure 4D:
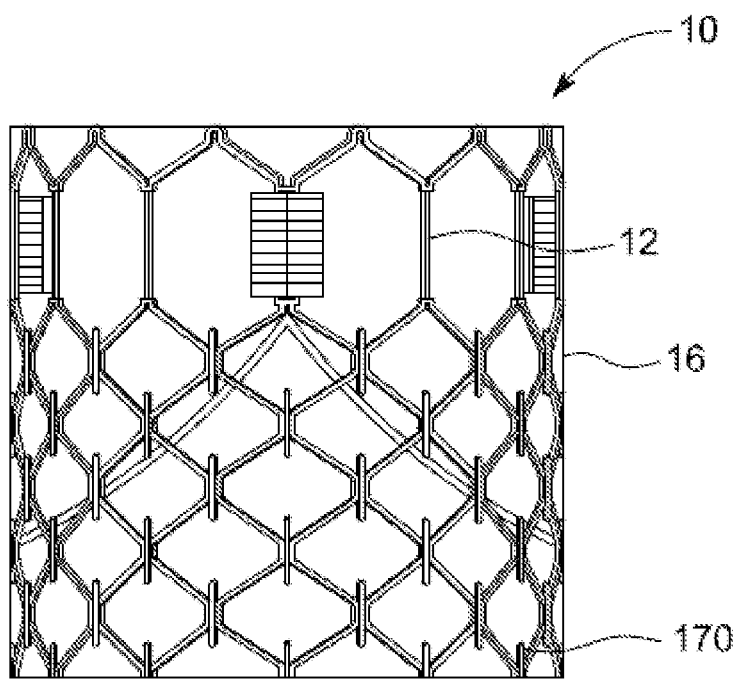

Turning to FIGS. 4A-4D, embodiments of the invention are illustrated. The illustrated valves are adapted to be implanted in the main pulmonary artery of a patient, although in other embodiments these embodiments can be adapted to be implanted in the other blood vessels, including the aorta and various native annuluses of the heart. The artificial valves 10 illustrated in FIGS. 4A-4E are illustrated to show the inflow end at the bottom of the figure with an outflow end at the top of the figure, thus forming a longitudinal axis between the inflow and outflow ends of the artificial valves 10. The inflow end is configured to receive antegrade blood flowing through circulatory system of a patient. In various embodiments, an artificial valve 10 comprises: a stent, or frame, 12, a leaflet structure 14, and an inner skirt 16. In some embodiments, the inner skirt 16 extends the full length of the frame 12 along the longitudinal axis of the artificial valve 10, such as illustrated in FIGS. 4A and 4B. However, in additional embodiments, such as illustrated in FIG. 4C, the tissue forming the inner skirt 16 may be longer than the frame 12 and can be wrapped over one or both ends of the frame 12 to form an outer skirt 18, thus reducing or eliminating exposure of the frame 12, when placed into the pulmonary trunk. Further embodiments may comprise various means to secure the artificial valve 10 in the pulmonary trunk of the patient. In some embodiments, such as illustrated in FIG. 4D, the securing means will be tissue engaging elements 170 protruding from the frame 12. These tissue engaging elements 170 can hold the frame 12 of the artificial valve 10 in place in the blood vessel of the patient.

Various embodiments of the artificial heart valve 10 are designed to be expandable, such that the frame 12 can be compressed into a collapsed configuration. As illustrated in FIGS. 4A-4E, various embodiments of an expandable, artificial heart valve by including a frame formed with angled struts to form a honeycomb-like structure. Additional details on expandable structures will be described below.

In some embodiments of the artificial heart, the materials used to construct these various elements can be permanent or stable to allow the removal and/or replacement of the artificial heart valve. In other embodiments, the materials used to construct these various elements can be chosen to allow the components to integrate with the body; for example, the tissue used for the skirt and/or leaflets may be regenerative tissue, which a body can integrate into the native blood vessel. Additionally, at least a portion of the frame of some embodiments can be selected from bioabsorbable materials to allow the degradation of the frame. Further embodiments may use both bioabsorbable materials for the frame and regenerative tissue for the leaflets and/or skirt, may allow the artificial heart valve to completely integrate and grow with a person's body. Details regarding materials and methods of construction of the various components described above will be described below. It should also be noted that various embodiments may use any combination of the above elements as the need arises to be effective in replacing the valve in a patient.

FIG. 4B illustrates a perspective view of the outflow end of an artificial valve 10 of some embodiments. As shown in FIG. 4B, some embodiments possess a leaflet structure 14, which comprises three leaflets 40, which can be arranged to collapse in a tricuspid arrangement, although additional embodiments can have a greater or fewer number of leaflets 40. In various embodiments, individual leaflets 40 are joined at commissures 122. In some embodiments, these commissures 122 may be sewn to the inner skirt 16, while other embodiments may pass commissures 122 through commissure window frames 30 in order to attach the leaflet structure 14 to the frame 12. Alternatively, certain embodiments may secure commissures 122 to both the inner skirt 16 and the frame 12 by sewing the commissures 122 to the inner skirt 16 and passing commissures 122 through commissure window frames 30. Additional details on joining leaflets and commissures will be described in detail below.

In additional embodiments, the inner skirt 16 is secured to the frame 12 by suturing. Suturing the inner skirt 16 to the frame 12 can be done as the only means of securing the inner skirt 16 to the frame 12, or suturing the inner skirt 16 to the frame 12 can be done in combination with securing the inner skirt 16 with the frame 12 using the commissure 122 of the leaflet structure 14. Suturing the inner skirt 16 to the frame 12 can be done by means known in the art, such that the inner skirt 16 is secured to the frame 12 and can allow expansion of the artificial valve 10 in some embodiments. Such suturing methods are described in U.S. Pat. No. 9,393,110, the disclosure of which is incorporated herein by reference in its entirety.

As illustrated in FIG. 4B, the lower edge of leaflet structure 14 of various embodiments desirably has an undulating, curved scalloped shape (suture line 154 shown in FIG. 4A tracks the scalloped shape of the leaflet structure). By forming the leaflets with this scalloped geometry, stresses on the leaflets are reduced, which in turn improves the durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form the leaflet structure 14, thereby allowing a smaller, more even crimped profile at the inflow end of the valve. The leaflets 40 can be formed of various natural or synthetic materials, including pericardial tissue (e.g., bovine pericardial tissue), biocompatible synthetic materials, or various other suitable natural or synthetic materials as known in the art and described in U.S. Pat. No. 6,730,118, which is incorporated by reference herein in its entirety. In additional embodiments, the leaflets 40 and leaflet structure 14 can be formed of regenerative tissue to allow integration of the leaflets into the tissue of the patient. Details regarding the use and manufacture of regenerative tissue are described below.

Figure 4E:
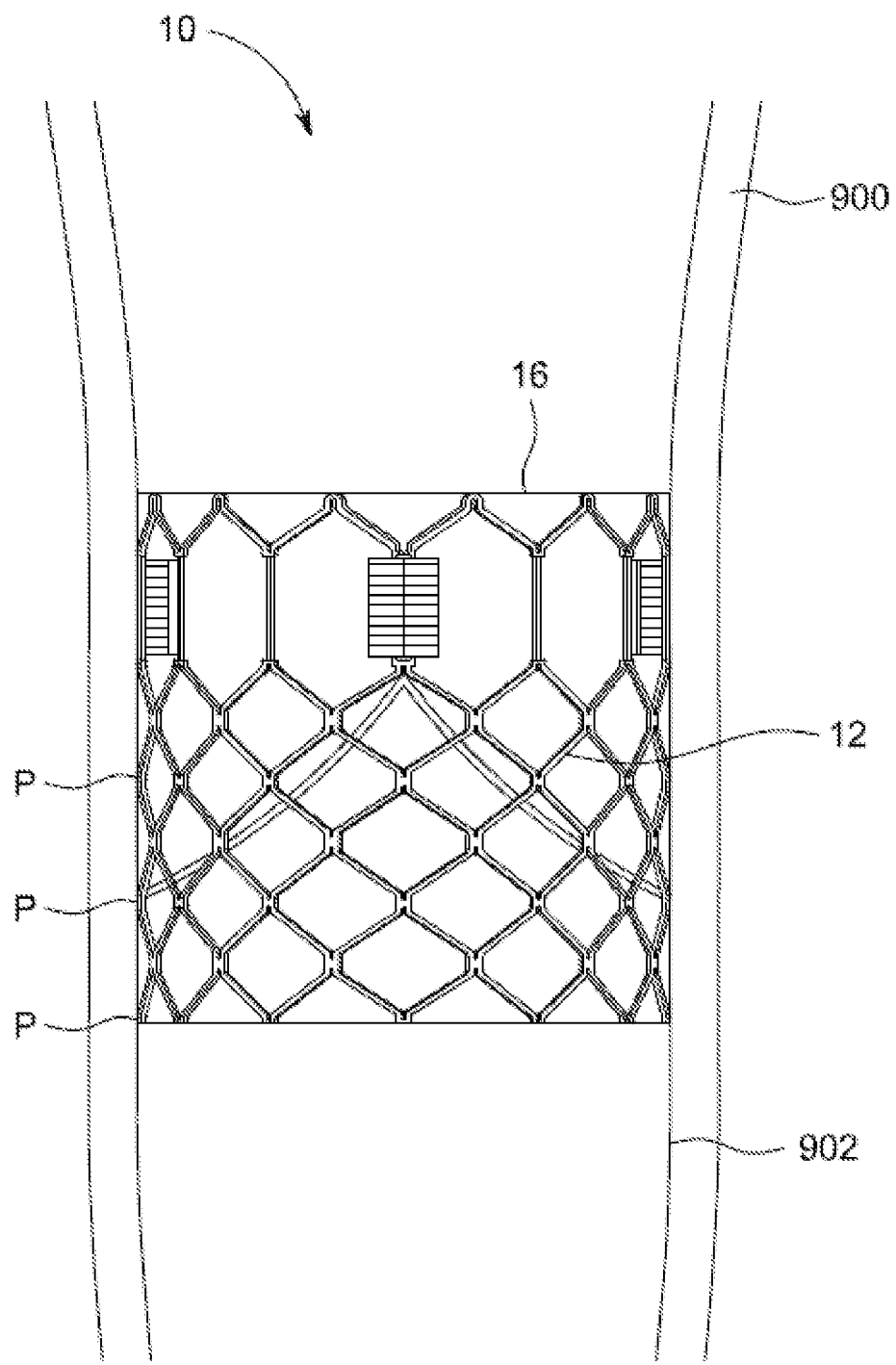
FIG. 4E illustrates a side view of an exemplary artificial heart valve deployed in a blood vessel in accordance with certain embodiments of the invention.

A deployed artificial valve 10 according to some embodiments is illustrated in FIG. 4E. In this figure the artificial valve 10 has been placed in a blood vessel 900, such as the main pulmonary artery, of a patient. The frame 12 contacts portions of the blood vessel wall 902 at points P. Points P in some embodiments will include tissue engaging elements 170 as describe above. In some embodiments, inner skirt 16, or in additional embodiments, the outer skirt 18, can contact the blood vessel wall 902 to form a tissue contact, which may encourage the integration of regenerative tissue used in the valve construction, including the inner skirt 16, outer skirt 18, and leaflets (not shown).

Figure 5A:
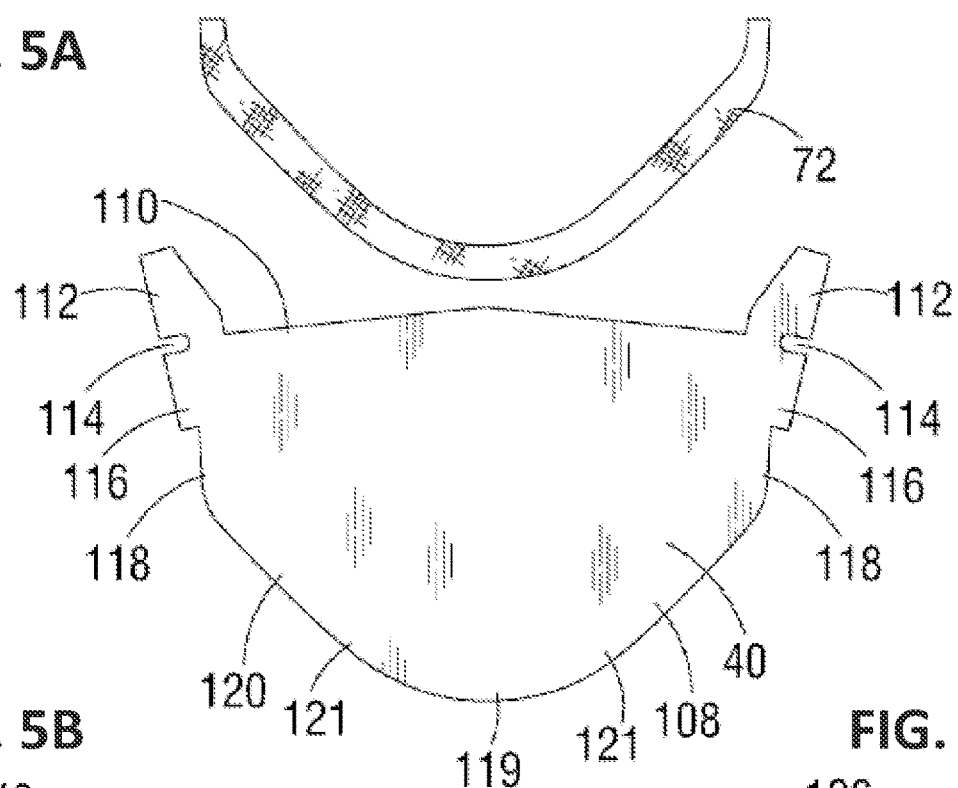
FIGS. 5A-5G illustrate the assembly of an exemplary leaflet structure in accordance with certain embodiments of the invention.
Figure 5B:
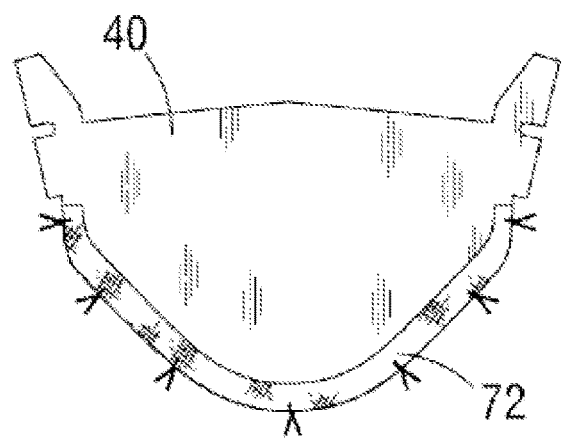

Turning now to FIGS. 5A-5G, the construction of a leaflet structure is detailed in accordance with various embodiments. As best shown in FIG. 5A, each leaflet 40 in the illustrated configuration has an upper (outflow) free edge 110 extending between opposing upper tabs 112 on opposite sides of the leaflet. Below each upper tab 112 there is a notch 114 separating the upper tab from a corresponding lower tab 116. The lower (inflow) edge portion 108 of the leaflet extending between respective ends of the lower tabs 116 includes vertical, or axial, edge portions 118 on opposites of the leaflets extending downwardly from corresponding lower tabs 116 and a substantially V-shaped, intermediate edge portion 120 having a smooth, curved apex portion 119 at the lower end of the leaflet and a pair of oblique portions 121 that extend between the axial edge portions and the apex portion. In some embodiments, the oblique portions can have a greater radius of curvature than the apex portion. In various other embodiments, each leaflet 40 can have a reinforcing strip 72 secured (e.g., sewn) to the inner surface of the lower edge portion 108, as shown in FIG. 5B.

Figure 5C:
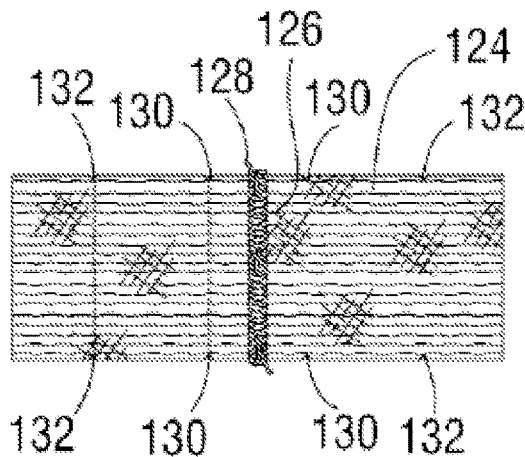

In embodiments, the leaflets 40 can be secured to one another at their adjacent sides to form commissures. A plurality of flexible connectors 124 (one of which is shown in FIG. 5C) can be used to interconnect pairs of adjacent sides of the leaflets and to mount the leaflets to the frame of various embodiments. The flexible connectors 124 can be made from natural or synthetic materials, such as regenerative tissue as described below or a piece of woven PET fabric. It should be noted that other synthetic and/or natural materials can be used. Each flexible connector 124 can include a wedge 126 extending from the lower edge to the upper edge at the center of the connector. The wedge 126 can comprise a non-metallic material, such as, but not limited to, rope, thread, suture material, or a piece of regenerative tissue, secured to the connector with a temporary suture 128. In various embodiments, the wedge 126 helps prevent rotational movement of the leaflet tabs once they are secured to the frame of certain embodiments. The connector 124 can have a series of inner notches 130 and outer notches 132 formed along its upper and lower edges.

Figure 5D:
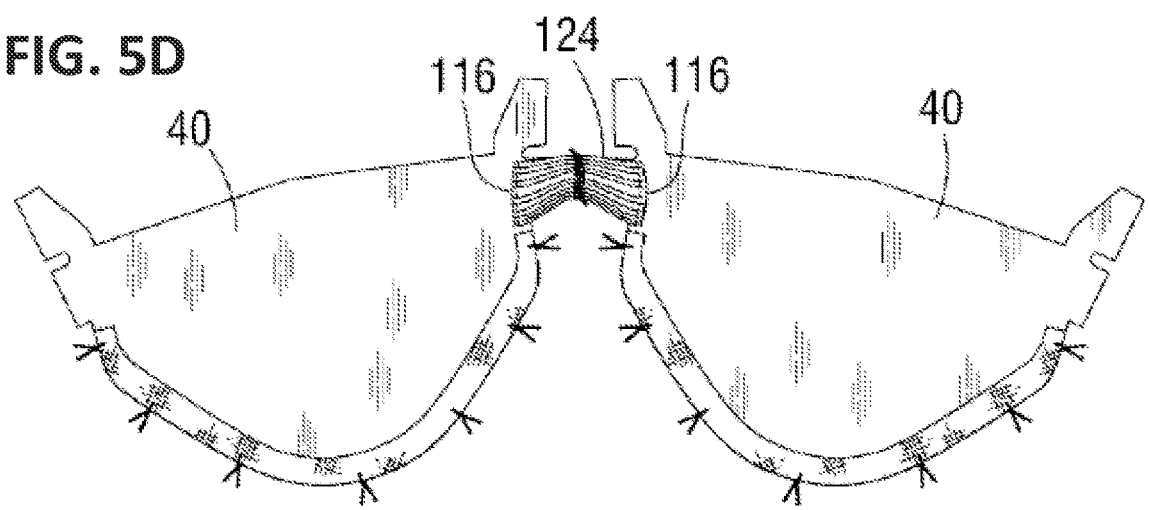
Figure 5E:
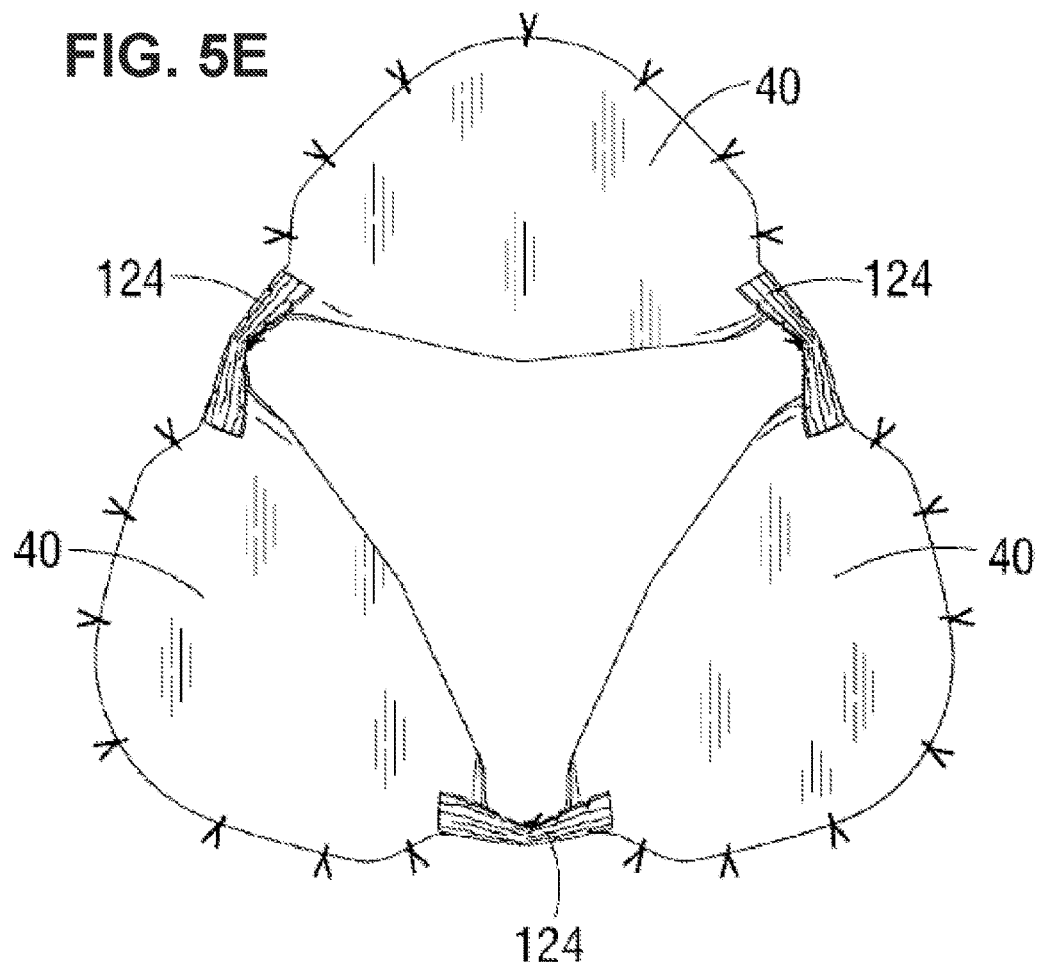

FIG. 5D shows embodiments where the adjacent sides of two leaflets 40 are interconnected by a flexible connector 124. In such embodiments, the opposite end portions of the flexible connector 124 can be placed in an overlapping relationship with the lower tabs 116 with the inner notches 130 aligned with the vertical edges of the tabs 116. Each tab 116 can be secured to a corresponding end portion of the flexible connector 124 by suturing along a line extending from an outer notch 132 on the lower edge to an outer notch 132 on the upper edge of the connector. Three leaflets 40 can be secured to each other side-to-side using three flexible connectors 124, as shown in FIG. 5E.

Figure 5F:
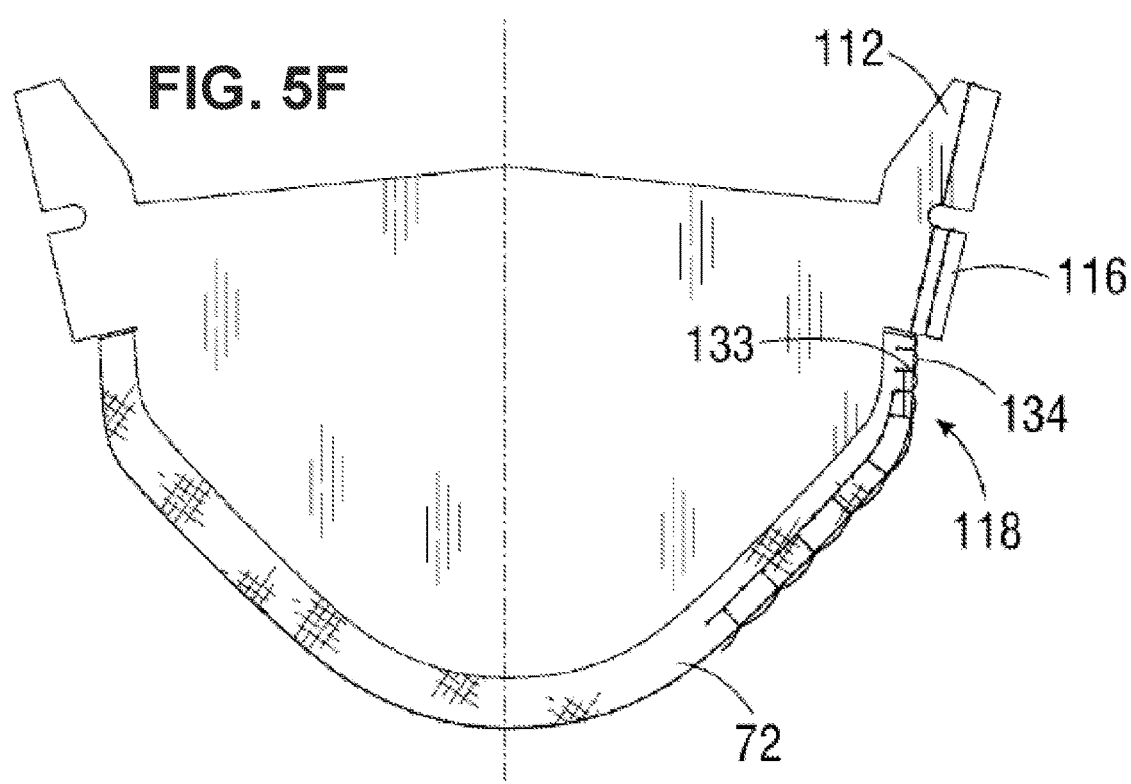
Figure 5G:
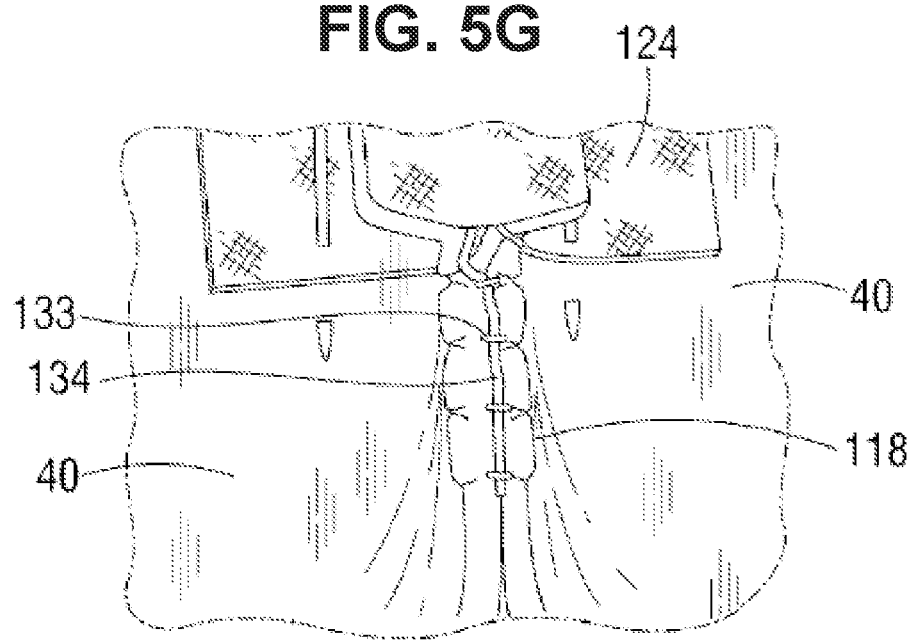

Referring now to FIGS. 5F and 5G, in various embodiments the adjacent sub-commissure portions 118 of two leaflets can be sutured directly to each other. In the example shown, suture material is used to form in-and-out stitches 133 and comb stitches 134 that extend through the sub-commissure portions 118 and the reinforcing strips 72 on both leaflets. The two remaining pairs of adjacent sub-commissure portions 118 can be sutured together in the same manner to form the assembled leaflet structure 14, which can then be secured to a frame in the following manner.

Figure 6A:
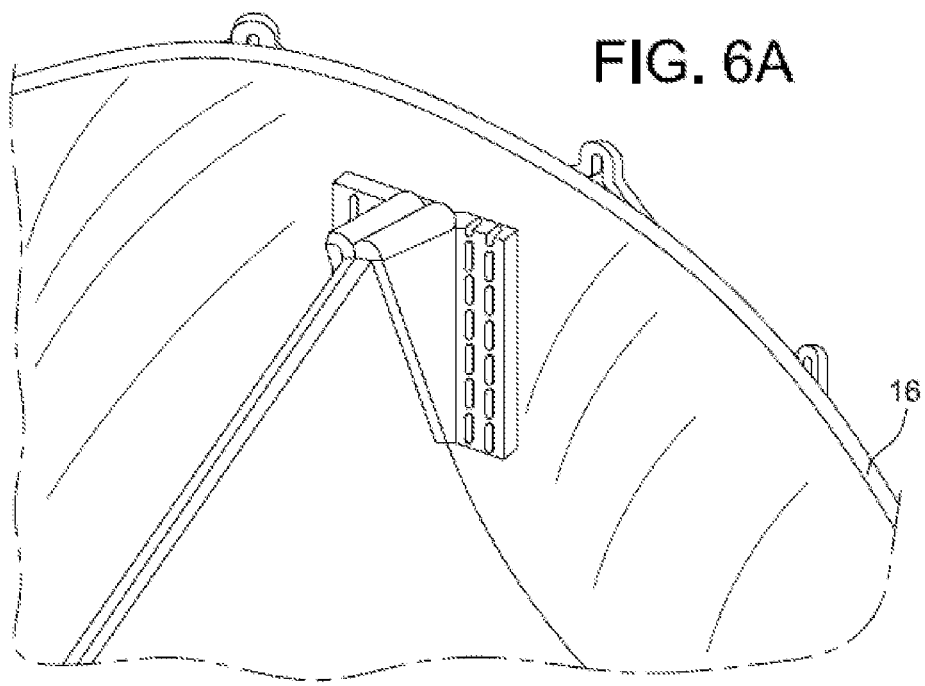
FIGS. 6A-6I illustrate the assembly of exemplary commissure portions of the leaflet structures in accordance with certain embodiments of the invention.
Figure 6B:
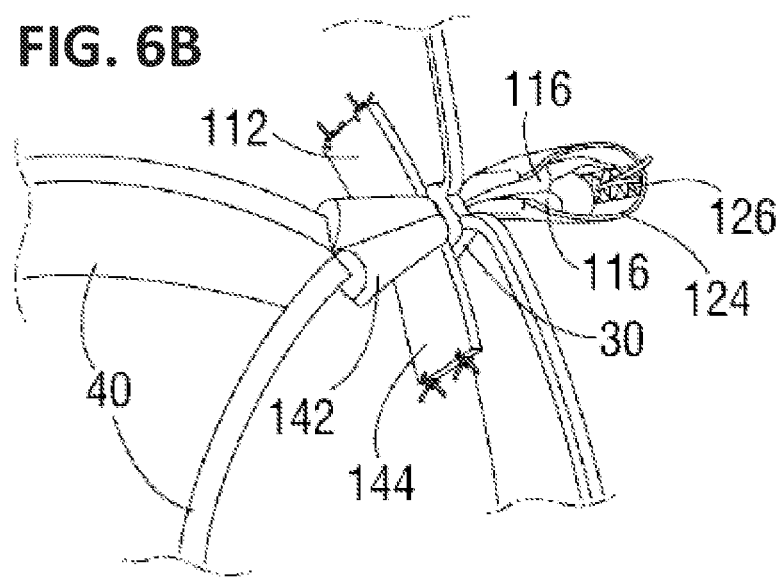
Figure 6C:
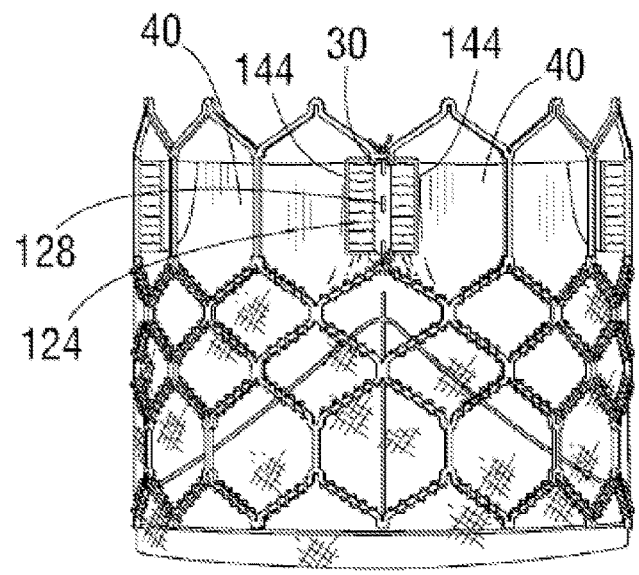

FIGS. 6A-6G show embodiments of one specific approach for securing the commissure portions 122 of the leaflet structure 14 to the commissure window frames 30 of the frame. First, as shown in FIG. 6A, the flexible connector 124 securing two adjacent sides of two leaflets 40 is folded widthwise and the upper tab portions 112 are folded downwardly against the flexible connector 124. As shown in FIGS. 6A and 6B, each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, as shown in FIG. 6B, the commissure tab assembly (comprised of a pair of lower tab portions 116 connected by connector 124) is inserted through the commissure window frame 30. FIG. 6C is a side view of the artificial valve 10 showing the commissure tab assembly extending outwardly through the commissure window frame 30.

Figure 6D:
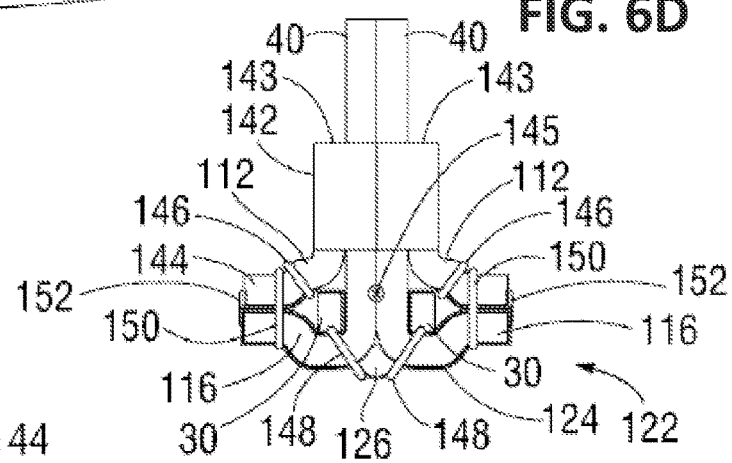
Figure 6E:
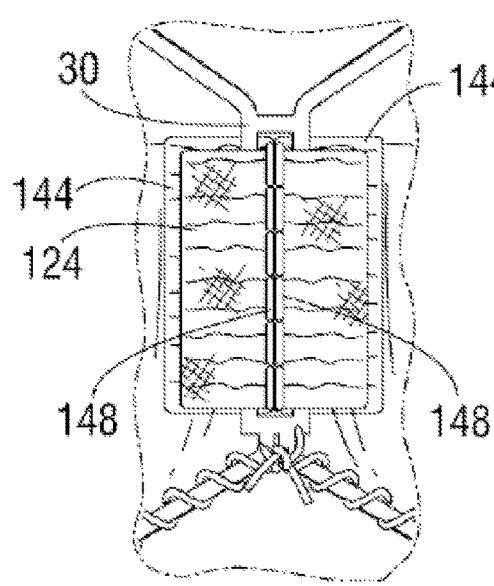
Figure 6G:
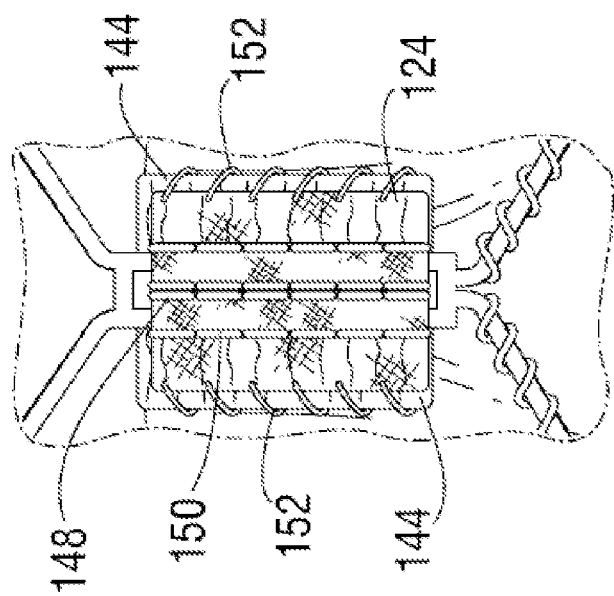
Figure 6F:
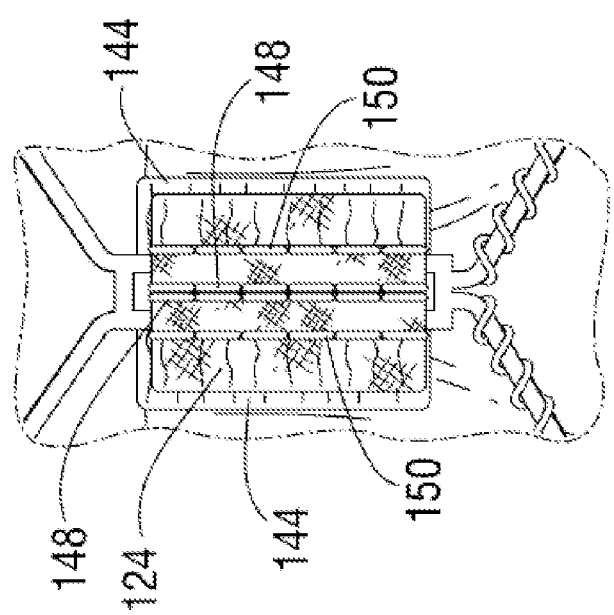

FIGS. 6D-6G illustrate a method to secure commissures to a frame according to some embodiments. In particular, FIG. 6D shows a cross-sectional view of a portion of the frame and leaflet structure showing the adjacent tab portions of two leaflets secured to a corresponding commissure window frame 30, while FIGS. 6E-6G illustrate perspective views of a portion of the frame and leaflet structure showing the adjacent tab portions of two leaflets secured to a corresponding commissure window frame 30. As shown in FIGS. 6D and 6E, the commissure tab assembly is pressed radially inwardly at the wedge 126 such that one of the lower tab portions 116 and a portion of the connector 124 is folded against the frame 12 on one side of the commissure window frame 30 and the other lower tab portion 116 and a portion of the connector 124 is folded against the frame 12 on other side of the commissure window frame 30. A pair of suture lines 148 are formed to retain the lower tab portions 116 against the frame 12 in the manner shown in FIG. 6D. Each suture line 148 extends through connector 124, a lower tab portion 116, the wedge 126, and another portion of connector 124. Then, as shown in FIGS. 6D and 6F, each lower tab portion 116 is secured to a corresponding upper tab portion 112 with a primary suture line 150 that extends through one layer of connector 124, the lower tab portion 116, another layer of connector 124, another layer of connector 124, and the upper tab portion 112. Finally, as shown in FIGS. 6D and 6G, the suture material used to form the primary suture line 150 can be used to further form whip stitches 152 at the edges of the tab portions 112,116 that extend through two layers of connector 124 sandwiched between upper tab portions 112 and lower tab portions 116.

As shown in FIGS. 6A and 6D, in embodiments, the folded down upper tab portions 112 form a double layer of leaflet material at the commissures. The inner portions 142 of the upper tab portions 112 are positioned flat and abutting the layers of the two leaflets 40 forming the commissures, such that each commissure comprises four layers of leaflet material just inside of the commissure window frames 30. This four layered portion of the commissures can be more resistant to bending, or articulating, than the portion of the leaflets 40 just radially inward from the relatively more rigid four layered portion. This causes the leaflets 40 to articulate primarily at inner edges 143 of the folded-down inner portions 142 in response to blood flowing through the valve during operation within the body, as opposed to articulating about the axial struts of the commissure window frames 30. Because the leaflets articulate at a location spaced radially inwardly from the commissure window frames 30, the leaflets can avoid contact with and damage from the frame. However, under high forces, the four layered portion of the commissures can splay apart about a longitudinal axis 145 (FIG. 6D) adjacent to the commissure window frame 30, with each inner portion 142 folding out against the respective outer portion 144. For example, this can occur when an artificial valve is compressed and mounted onto a delivery shaft, allowing for a smaller crimped diameter. The four layered portion of the commissures can also splay apart about axis 145 when the balloon catheter is inflated during expansion of the valve, which can relieve some of the pressure on the commissures caused by the balloon and so the commissures are not damaged during expansion.

Figure 6H:
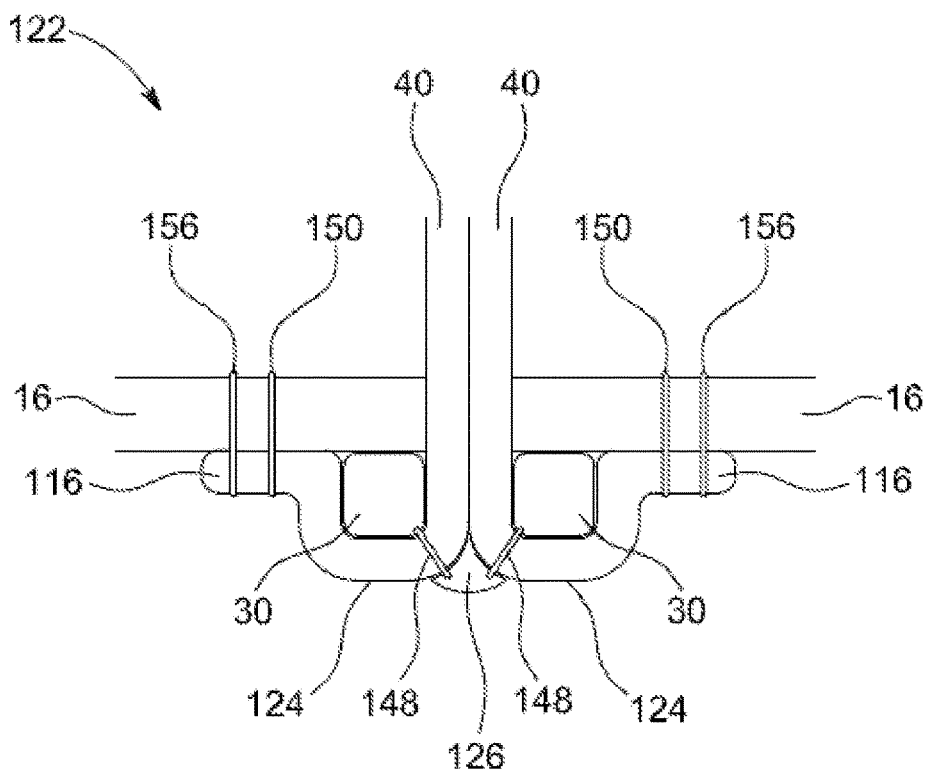
Figure 6I:
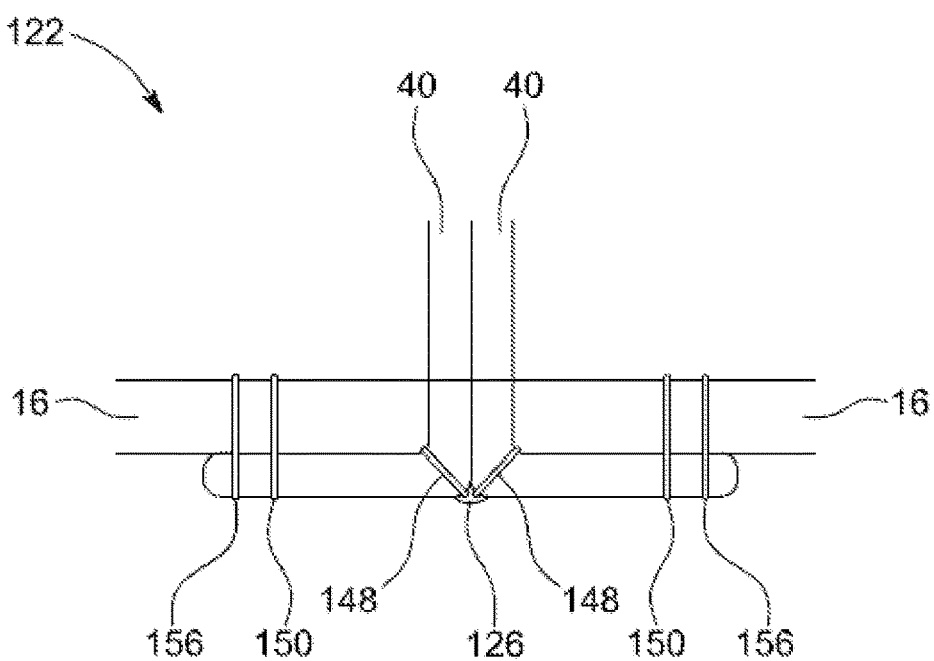

Additional embodiments may be used to secure the commissures by other methods. FIGS. 6H and 6I illustrate cross-sectional views of embodiments of commissures that utilize different methods to secure the commissures to a frame of certain embodiments. Specifically, FIG. 6H illustrates a commissure tab assembly passing through a commissure window frame 30 and pressed radially inwardly at the wedge 126 such one lower tab portion 116 and a portion of the connector 124 is folded against the inner skirt 16 on one side of the commissure window frame 30. A pair of suture lines 148 are formed to retain the lower tab portions 116 against the inner skirt 16. Each suture line 148 extends through connector 124, a lower tab portion 116, the wedge 126, and another portion of connector 124. Then, each lower tab portion 116 is secured to the inner skirt 16 with a primary suture line 150 that extends through one layer of connector 124, the lower tab portion 116, another layer of connector 124, and the inner skirt 16. Additional suture lines 156 may be applied to the connector-tab-skirt assembly to provide additional strength and/or secure extra tissue that may be present.

FIG. 6I illustrates embodiments where the commissure tab assembly passes through an inner skirt 16 and presses radially inwardly at the wedge 126 such that the commissure tab assembly attaches to the inner skirt and does not attach to a frame. In such embodiments, each lower tab portion 116 is secured to the inner skirt 16 with a primary suture line 150 that extends through one layer of connector 124, the lower tab portion 116, another layer of connector 124, and the inner skirt 16. A pair of suture lines 148 may also be present to retain the lower tab portions 116 against the inner skirt 16. Each suture line 148 extends through connector 124, a lower tab portion 116, the wedge 126, and another portion of connector 124. In some embodiments, each suture line 148 may further extend through the inner skirt 16. Then, additional suture lines 156 may be applied to the connector-tab-skirt assembly to provide additional strength and/or secure extra tissue that may be present.

In various embodiments, after all commissure tab assemblies are secured to respective commissure windows, the lower edges of the leaflets 40 between the commissure tab assemblies can be sutured to the inner skirt 16. Details on stitching leaflets to the inner skirt of an artificial valve can be found in U.S. Pat. No. 9,393,110 to Levi et al., the disclosure of which is incorporated herein by reference in its entirety.

In various embodiments, the tissue utilized for the inner skirt and leaflet structure, including leaflets, is regenerative tissue, such that the artificial valve will integrate into the body of the individual receiving the artificial valve. Suitable materials will allow the patient's body to fully integrate the material, such that the material will continue growing with the body of the patient. Such material will allow the valvular structure and skirt to grow in a concomitant manner as the patient's heart grows such that replacement is not required. Regenerative materials may include decellularized tissue from a natural source, which may require ligation of branching blood vessels. Alternatively, some embodiments will use an artificial construct to form the regenerative tissue, which are engineered and may not require steps to ligate portions. Examples of artificial tissue constructs include, but are not limited to tissue generated from polyglactin, collagen, and polyglycolic acid, which are formed into scaffolds or constructs. In some embodiments using artificial constructs, the artificial constructs include extracellular matrix proteins to allow integration of the tissue. Examples of regenerative tissue and methods of constructing these materials can be found in U.S. Pat. No. 6,666,886 to Tranquillo et al. and U.S. Pat. No. 9,657,265 to Dahl et al., the disclosures of which are incorporated herein by reference in their entireties.

In embodiments using polyglycolic acid scaffolds, the polyglycolic acid scaffolds are bioabsorbable and the extracellular matrix proteins will allow seeding of the host's tissue in order to incorporate the regenerative tissue into the patient's body. Examples of suitable extracellular matrix proteins include, but are not limited to, hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof. In some embodiments, polyglycolic acid scaffolds will include the extracellular matrix proteins within the scaffold, while in other embodiments, extracellular matrix proteins will cover the polyglycolic acid scaffolds with extracellular matrix proteins. In yet further embodiments, the extracellular matrix proteins will be both within the polyglycolic acid scaffold and coating the polyglycolic acid scaffolds.

In certain embodiments, the skirt will merge with the pulmonary trunk tissue and provide an anchor point for the leaflets and provide structural support for the valve. Various embodiments will use different regenerative tissues for the skirt and the leaflets to provide an improved integration of the tissue. Such combinations may improve the flexibility of the leaflets, while maintaining more rigidity or strength in the skirt, which incorporates as a blood vessel wall.

Figure 7F:
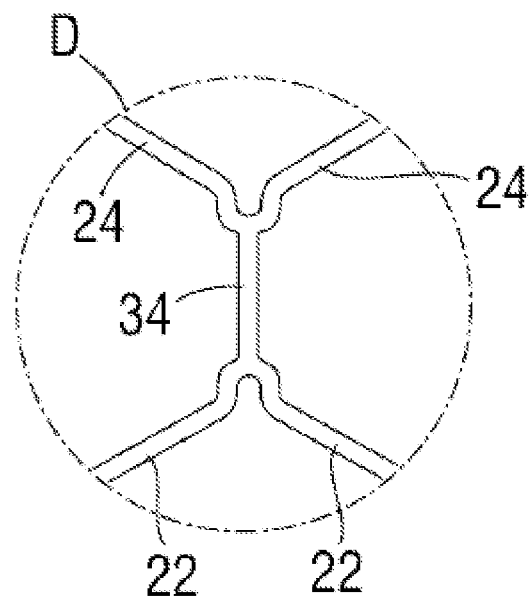
Figure 7G:
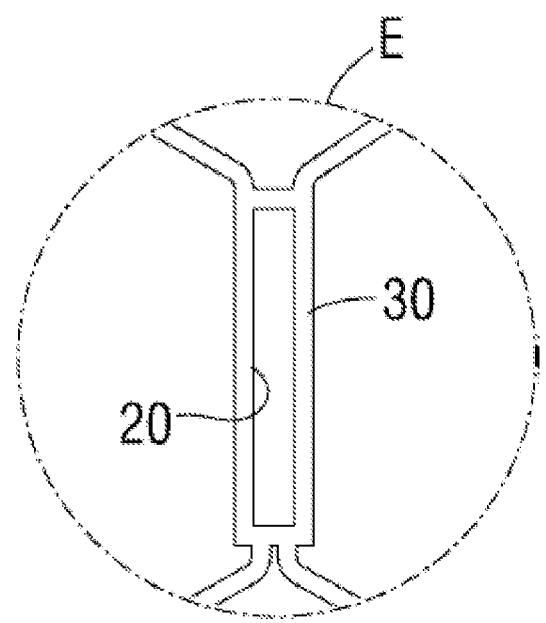

Referring to FIGS. 7A and 7B, a frame 12 in accordance with certain embodiments is shown. The frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 7C-7G are enlarged views of the portions of the frame 12 identified by letters A, B, C, D and E, respectively, in FIG. 7B.

In accordance with many embodiments, each commissure window frame portion 30 mounts to a respective commissure of the leaflet structure 14. As can be seen each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 7A) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large as compared to intermediate openings 38 and/or lower openings 36 and are sized to allow portions of the leaflet structure 14 to protrude, or bulge, into and/or through the openings 40 when the frame 12 is crimped in order to minimize the crimping profile.

Figure 14A:
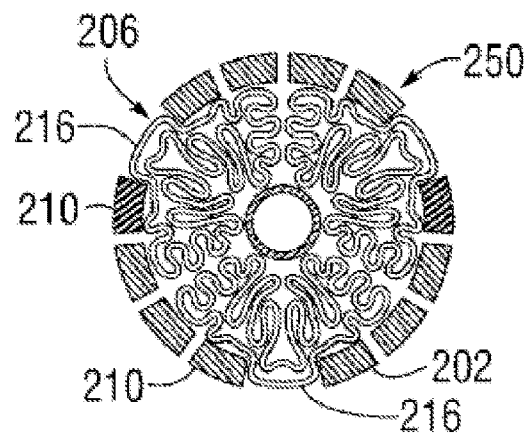
FIGS. 14A and 14B illustrate cross-sectional views of exemplary artificial heart valves in compressed states and mounted on catheters in accordance with certain embodiments of the invention.
Figure 14B:
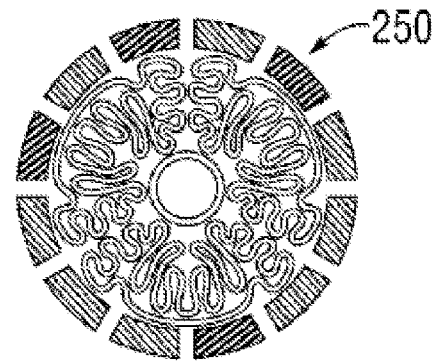

As best shown in FIG. 7D, in various embodiments the lower end of the strut 31 is connected to two struts 28 at a node or junction 44, and the upper end of the strut 31 is connected to two struts 32 at a node or junction 46. In some embodiments, the strut 31 can have a thickness S1 that is less than the thicknesses S2 of the junctions 44 and 46. The advantage of this differential thickness is illustrated below in FIGS. 14A-14B showing a portion of the frame 12 in a crimped state.

In many embodiments, the frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles 42a, 42b, 42c, 42d, 42e between struts. The larger the angle, the greater the force required to open (expand) the frame. When the frame 12 is in its compressed state (e.g., mounted on a balloon). The vertical distance between the ends of the struts is greatest when the frame is compressed, providing a relatively large moment between forces acting on the ends of the strut in opposite directions upon application of an opening force from inflation of the balloon (or expansion of another expansion device). When the frame expands radially, the vertical distance between the ends of the strut decreases. As the vertical distance decreases, so does the moment between forces. Hence, it can be seen that a relatively greater expansion force is required as the vertical distance and the moment between the ends of the strut decreases. Moreover, strain hardening (stiffening) at the ends of the strut increases as the frame expands, which increases the expansion force required to induce further plastic deformation at the ends of the strut. As such, in various embodiments, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are at least 120 degrees or greater when the frame is expanded to its functional size.

Also, as can be seen in FIG. 7B, in some embodiments, the openings 36 of the lowermost row of openings in the frame are relatively larger than the openings 38 of the two intermediate rows of openings. This configuration allows the frame, when crimped, to assume an overall tapered shape that tapers from a maximum diameter at the outflow end of the valve to a minimum diameter at the inflow end of the valve. When crimped, the frame 12 has a reduced diameter region extending along a portion of the frame adjacent the inflow end of the frame. The diameter of the lower portion region is reduced compared to the diameter of the upper portion of the frame. When the valve is deployed, the frame can expand to the cylindrical shape shown in FIG. 7A.

In some embodiments, the frame may be constructed of a material, such that the frame remains intact in the body when introduced, while other embodiments may be constructed of materials that are bioabsorbable, such that the frame eventually degrades in the body. Materials which can be used to construct the frame are discussed in detail below. When constructed of a plastically-expandable material, the frame 12 (and thus the valve 10) can be crimped to a radially compressed state on a delivery catheter and then expanded inside a patient by an inflatable balloon or equivalent expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

As noted above, in various embodiments, the frame 12 will include tissue engaging elements 170 to secure the artificial valve 10 to the blood vessel of a patient. FIGS. 8A-8R illustrate various possible tissue engaging elements that may be placed on frame 12. In the embodiment of FIG. 8A, the tissue engaging element 170 comprises a shaft 450 formed with a diamond-shaped window 451 near its distal tip 452, which can be sharp enough to penetrate tissue. In such embodiments, the shape may be set so that window 451 is biased toward being open in an expanded configuration as shown in FIG. 8A. Prior to delivery of the device, window 451 may be pinched closed and a bioabsorbable glue 455 may be injected into window 451 to hold it in a closed configuration as shown in FIG. 8B. Upon deployment of the device, the distal tip 452 can penetrate the native tissue, e.g. blood vessel wall, as shown in FIG. 8C. The glue 455 within window 451 maintains it in a closed configuration for a period of time to allow the operator to reposition or remove the device if necessary. If left in position, the glue 455 erodes, allowing the window 451 to reopen into the expanded configuration which will retain the tissue engaging element 170 in the tissue as shown in FIG. 8D.

In the embodiment shown in FIGS. 8E-8H, the tissue engaging element 170 comprises an arrowhead-shaped tip 453 having two or more wings 454 biased to be angled radially outward and pointing in a proximal direction as shown in FIG. 8E. A bioabsorbable glue or coating 455 can be applied over the arrowhead tip 453 to hold the wings 454 in a radially contracted configuration as shown in FIG. 8F. In the contracted configuration, the device 100 is deployed such that the tissue engaging element 170 pierces the native tissue as shown in FIG. 8G. The bioabsorbable coating 455 then erodes gradually until it allows the wings 454 to return to the laterally expanded configuration shown in FIG. 8H, thus retaining the tissue engaging element 170 in the tissue.

A further embodiment is shown in FIGS. 8I-8L. In this embodiment, the tissue engaging element 170 comprises a helical tip 456 in an unbiased state. A bioabsorbable coating 455 may be used to retain the helical tip 456 in a straightened configuration as shown in FIG. 8J. The tissue engaging element 170 can penetrate the tissue in the contracted configuration, and when the bioabsorbable coating 455 erodes sufficiently to allow the helical tip 456 to return to its deployed configuration, the tissue engaging element 170 can be retained in the tissue.

FIGS. 8M-8R are enlarged side views of embodiments of additional tissue engaging elements that can be incorporated on various device structures (referred collectively as "ST"), such struts, connectors, posts, arms, and/or ribs which may be incorporated into device features, such as the anchoring member 110 or valve support 120. For example, the additional tissue engaging elements may comprise one or more cut-out protrusions 350 (FIGS. 8M and 8N) in place of or in addition to tissue engaging elements 170. In a collapsed or straightened configuration, as shown by the side view of FIG. 8O, cut-out protrusion 350 maintains low relief relative to the surface of structure ST to maintain a low profile during delivery. As the device 100 expands and structure ST changes to its deployed configuration (e.g. a curvature as shown in FIG. 8P), the protrusion separates from the ST to a higher relief. The protrusion 350 may also be configured to grab subannular tissue, pulling the cut-out protrusions even farther away from structure ST. The device structures ST may also be shaped to include sharp protrusions 352 along one or more of its edges or faces, as illustrated in FIG. 8Q, or may also include pointed scale-like protrusions 354, as shown in FIG. 8R.

Suitable plastically-expandable materials that can be used to form a transcatheter frame 12 and tissue engaging elements 170 that remains intact in a body in accordance with various embodiments include, without limitation, stainless steel, a nickel based alloy (e.g., a cobalt-chromium or a nickel-cobalt-chromium alloy), Nitinol, certain polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N®/1TNS R30035 alloy comprises 35% nickel, 35% cobalt, 20% chromium, and 10% molybdenum, by weight.

However, some embodiments possess bioabsorbable frames and tissue engaging elements which may be constructed of suitable materials including, without limitation, poly(L-lactide) (PLLA), poly(L-lactide) (PDLA), polyglycolide (PGA), poly(L-lactide-co-glycolide) (PLGA), polyhydroxyalkanoate (PHA), polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate; polyhydroxyvalerate, poly-orthoesters, poly-anhydrides, polyiminocarbonate, and copolymers and combinations thereof.

Additionally, some embodiments with bioabsorbable frames will be reinforced with reinforcing compositions. Reinforcing compositions for bioabsorbable frames can include magnesium and magnesium alloys. Magnesium and its alloys are biocompatible, bioabsorbable and easy to mechanically manipulate presenting an attractive solution for reinforcing bioabsorbable polymer stents. Radiological advantages of magnesium include compatibility with magnetic resonance imaging (MRI), magnetic resonance angiography and computed tomography (CT). Vascular stents comprising magnesium and its alloys are less thrombogenic than other bare metal stents. The biocompatibility of magnesium and its alloys stems from its relative non-toxicity to cells. Magnesium is abundant in tissues of animals and plants, specifically Mg is the fourth most abundant metal ion in cells, the most abundant free divalent ion and therefore is deeply and intrinsically woven into cellular metabolism. Magnesium-dependent enzymes appear in virtually every metabolic pathway is also used as a signaling molecule. Magnesium alloys which are bioabsorbable and suitable for reinforcing bioabsorbable polymer stents include alloys of magnesium with other metals including, but not limited to, aluminum and zinc. In one embodiment, the magnesium alloy comprises between about 1% and about 10% aluminum and between about 0.5% and about 5% zinc.

The magnesium alloys of the present invention include but are not limited to Sumitomo Electronic Industries (SEI, Osaka, Japan) magnesium alloys AZ31 (3% aluminum, 1% zinc and 96% magnesium) and AZ61 (6% aluminum, 1% zinc and 93% magnesium). The main features of the alloy include high tensile strength and responsive ductility. Tensile strength of typical AZ31 alloy is at least 280 MPa while that of AZ61 alloy is at least 330 MPa.

Reinforcing bioabsorbable polymeric materials with bioabsorbable magnesium materials can be accomplished with one of the methods including, but not limited to, the use of bioabsorbable magnesium wire, magnesium fibers either wound around or within a polymeric stent or impregnated within a bioabsorbable polymeric frame.

In certain embodiments, the specific material used for the frame and tissue engaging elements is chosen to allow absorption of the frame by the body of the patient undergoing valve replacement. The absorption properties of these materials may be selected based on time a body absorbs or incorporates the particular material. Thus, different materials or combinations of materials may be used to ensure that the frame dissolves after regenerative tissue integrates with the patient's tissue. As such, if integration of the tissue occurs in less than one year, then frame materials that will hold the valve's integrity for more than one year will be desirable. For example, if integration of the regenerative tissue occurs in a 6-12 month time frame, the frame should hold its integrity for at least one year and be fully absorbed by the body over the period of 3, 6, 9, or 12 months. Thus, at the end of 24 months, the artificial valve will be fully integrated into the body with very little or no remnants of the frame remaining.

Figure 9B:
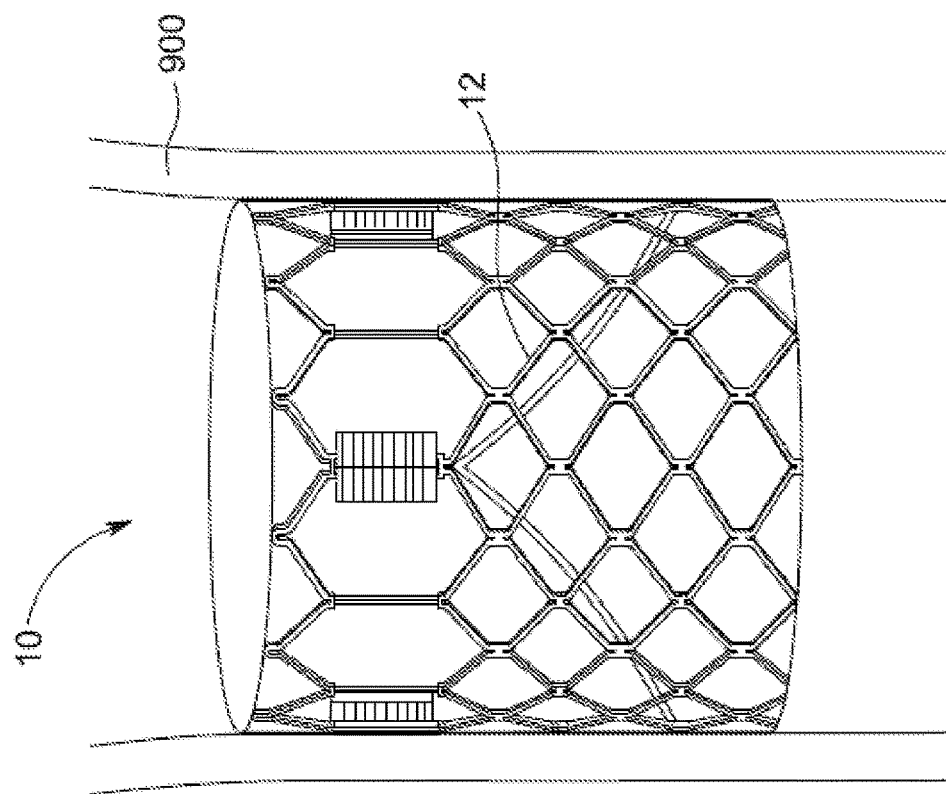
FIG. 9A-9D illustrate an example of the integration of regenerative tissue and the bioabsorption of a bioabsorbable materials of an artificial heart valve in accordance with certain embodiments of the invention.
Figure 9A:
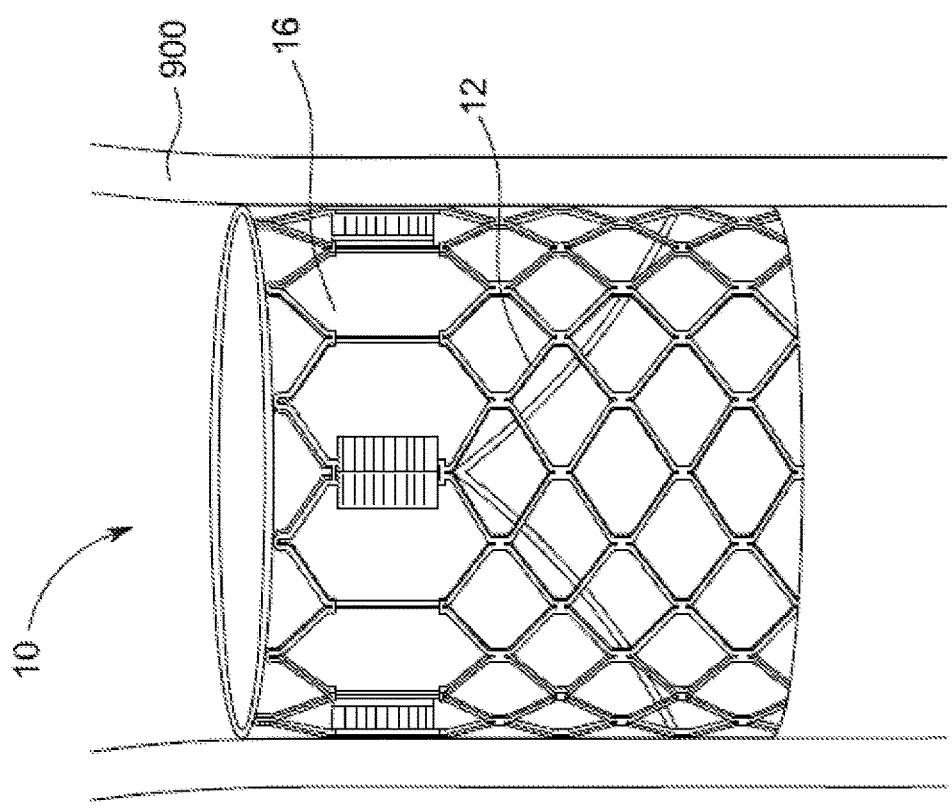
Figure 9D:
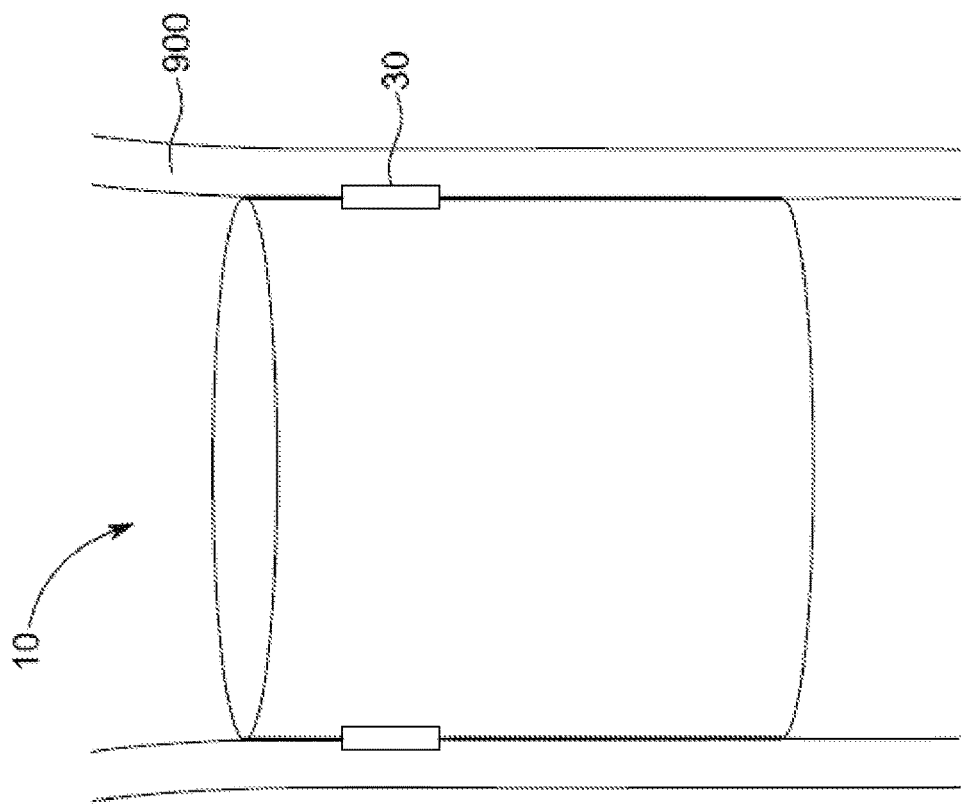
Figure 9C:
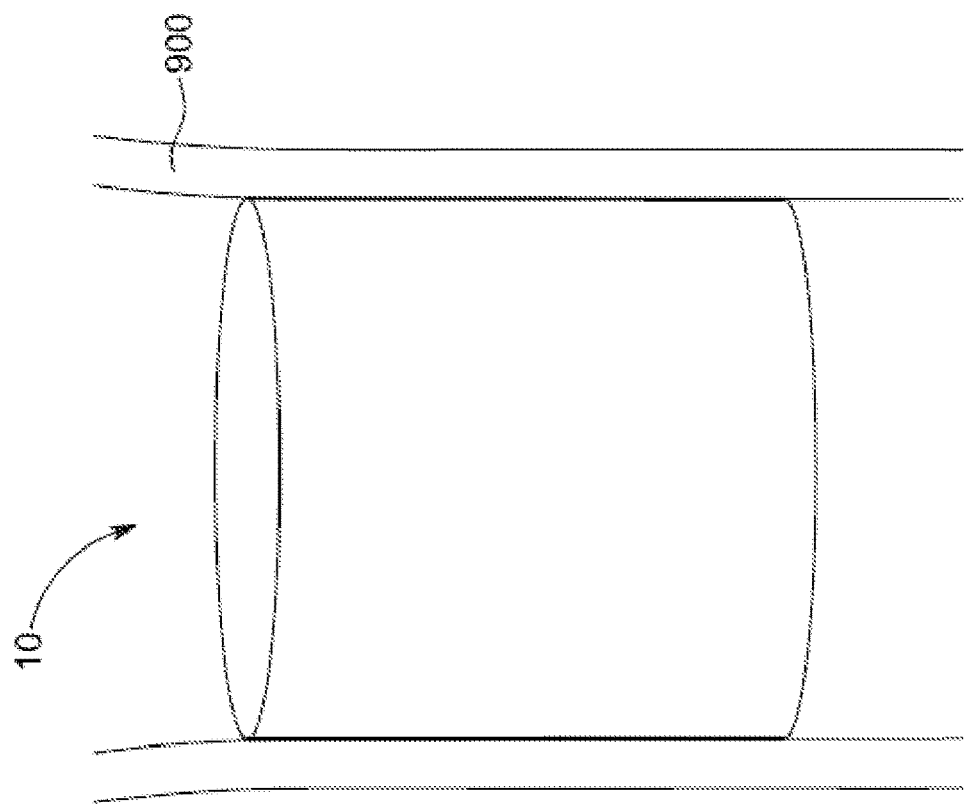

FIGS. 9A-9D illustrate an example of the process of integration and absorption of the frame. FIG. 9A illustrates an embodiment of an artificial valve 10 implanted in the pulmonary trunk of a patient. As seen in this figure, the frame 12 is intact and the inner skirt tissue has not integrated with the patient's tissue. In FIG. 9B, the tissue portions, including the inner skirt 16, has integrated with the patient's tissue, while the frame is still present to provide support for the artificial valve 10 during this process. FIGS. 9C and 9D illustrate a full integration of the artificial valve 10, where the tissue has integrated and the frame has been absorbed.

Further, some embodiments will utilize a combination of non-bioabsorbable materials and bioabsorbable materials in the frame. Using a combination of bioabsorbable and non-bioabsorbable materials will allow some parts of the frame to degrade, while certain portions will remain intact in the body of the patient to continue to provide support over time. Certain embodiments are made of a bioabsorb able frame comprising non-bioabsorb able commissure windows. In embodiments having non-bioabsorb able commissure windows and a bioabsorb able frame, the frame will degrade over time, but the commissure windows will remain permanent in the body to provide additional support to the leaflets by permanently securing the commissures of the valvular structure. FIG. 9D illustrates an embodiment where the tissue has fully integrated with the patient's body, the frame has been absorbed, and the commissure window frames 30 are made of a non-bioabsorbable material and remain present in the body after the frame has been fully absorbed.

Additional embodiments will include growth factors in the frame and tissue engaging elements. Growth factors can stimulate or promote the integration of the regenerative tissue with the patient. Examples of growth factors that can be used in embodiments include, but are not limited to, transforming growth factor alpha (TGF-alpha), transforming growth factor beta (TGF-beta), basic fibroblast growth factor (bFGF), vascular epithelial growth factor (VEGF), and combinations thereof. In certain embodiments, growth factors are incorporated within the frame material, while some embodiments have the growth factors coating the frame material. In additional embodiments, the growth factors are both incorporated in the frame material and coating the frame material. The growth factors can be formulated to release over time or may release as the frame degrades during the bioabsorption process.

Figure 10A:
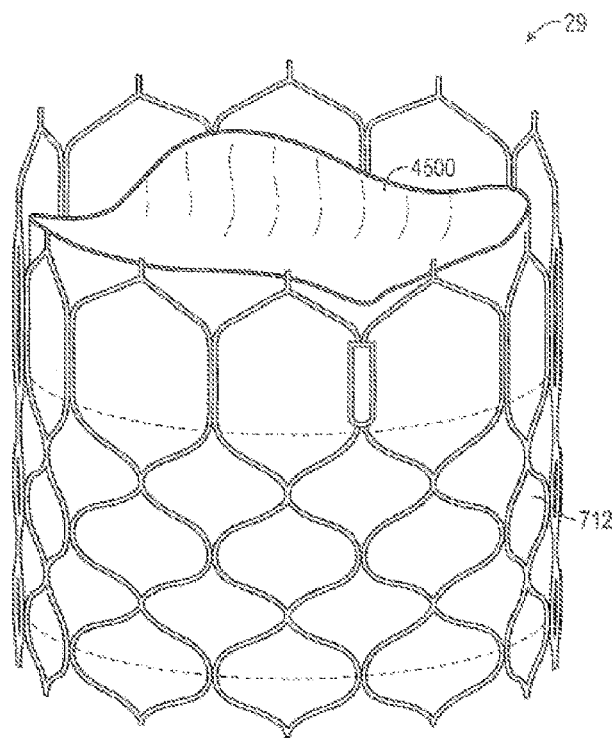
FIG. 10A illustrates a cylindrical frame of an artificial heart valve in accordance with certain embodiments of the invention.
Figure 10B:
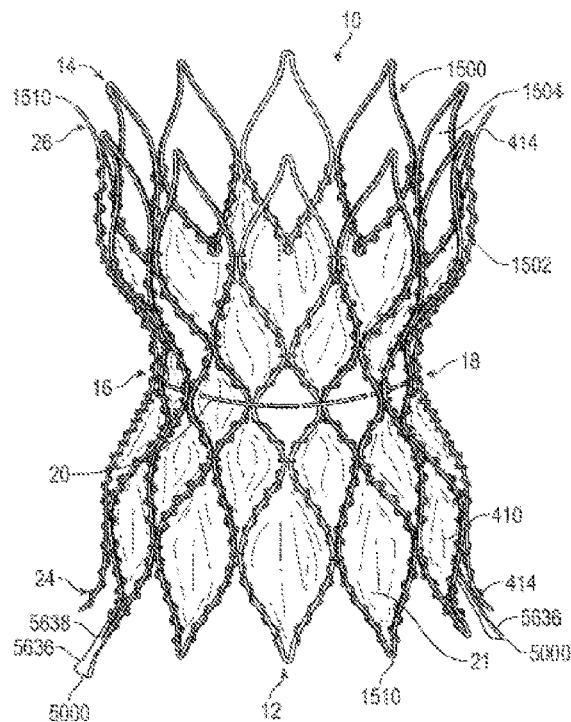
FIG. 10B illustrates an hourglass shaped frame of an artificial heart valve in accordance with certain embodiments of the invention.

Although specific artificial valve shapes have been shown in Figures thus far, it will be understood that these shapes may vary depending on the specific application. Turning now to FIGS. 10A and 10B, various exemplary shapes of artificial valves in accordance with embodiments are illustrated. As illustrated above and in FIG. 10A, frames can be cylindrical in nature in order to fit in the pulmonary trunk of a patient. Cylindrical frames may be suitable for placement in a blood vessel at a point away from the native valve, such that the artificial valve supplements a faulty or defective valve in the patient. However, some embodiments will utilize an hourglass-shaped frame for the artificial valve, as illustrated in FIG. 10B. Hourglass frames may provide certain advantages for artificial valves, such that an hourglass-shaped valve may be placed at the native position of the valve. In this way, and hourglass valve may replace the native valve rather than supplement the valve. The hourglass valve accomplishes this task by being placed at a position where waist of the hourglass frame provides space for the native valve flaps.

Figure 11A:
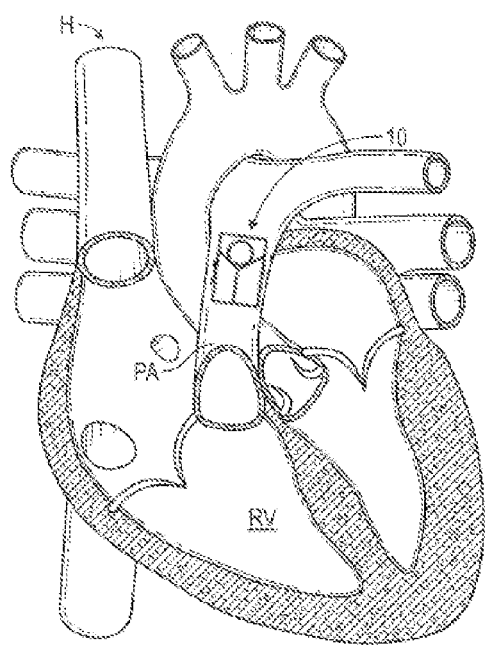
FIGS. 11A and 11B illustrate possible placement locations in the pulmonary artery of an artificial heart valves in accordance with certain embodiments of the invention.
Figure 11B:
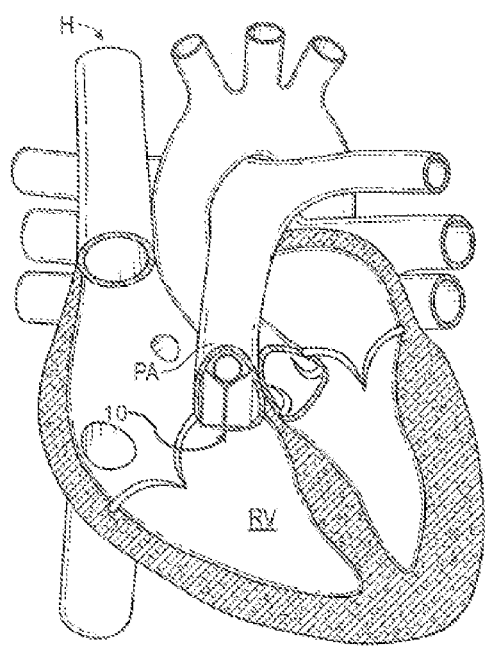

Examples of the placement of the artificial valve 10 in the main pulmonary artery PA are illustrated in FIGS. 11A-11B. In FIGS. 11A-11B, a cutaway of a heart H is shown in the systolic phase. When the heart is in the systolic phase, the pulmonic valve (not shown) opens, and blood flows from the right ventricle RV and through the pulmonary artery PA. FIG. 11A illustrates the position of an artificial valve 10 deployed downstream of the native pulmonic valve, in accordance with various embodiments. In FIG. 11B, the artificial valve 10 of some embodiments is deployed at the site of the pulmonic valve, thus replacing the native valve of the patient.

Figure 12:
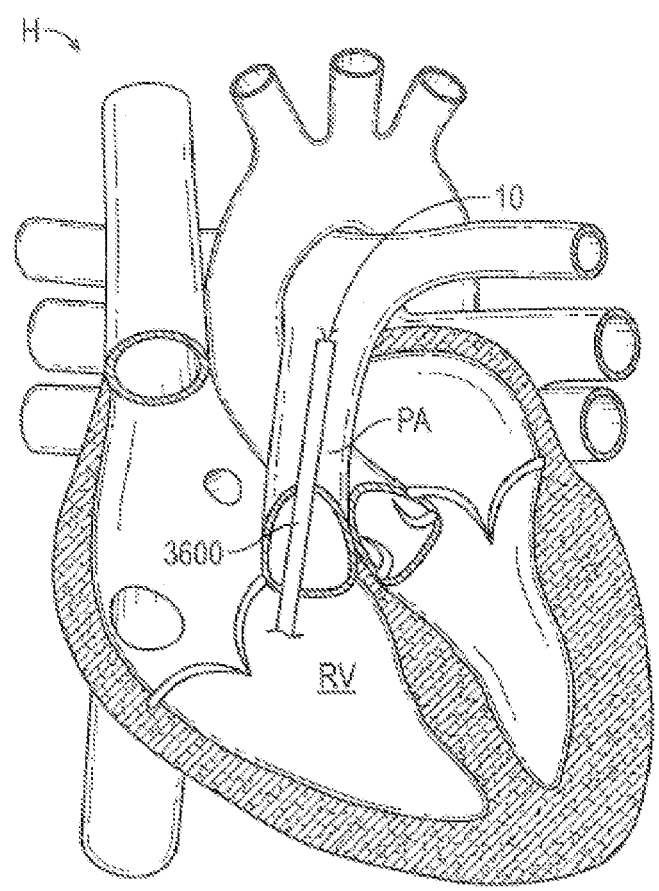
FIG. 12 illustrates a cutaway view of the human heart in a systolic phase showing an exemplary path to implant an artificial heart valve using a catheter in accordance with certain embodiments of the invention.

Methods of treating a patient (e.g., methods of treating heart valve dysfunction/regurgitation/disease/etc.) may include a variety of steps, including steps associated with introducing and deploying an artificial valve in a desired location/treatment area. Some embodiments are placed in a patient through surgical means, while other embodiments are placed in position by transcatheter insertion. For example, FIG. 12 illustrates an artificial valve of various embodiments being deployed by a catheter 3600. The artificial valve 10 can be positioned and deployed in a wide variety of different ways. Access can be gained through the femoral vein or access can be percutaneous. Generally, any vascular path that leads to the pulmonary artery may be used. In one exemplary embodiment, a guidewire followed by a catheter 3600 is advanced to the pulmonary artery PA by way of the femoral vein, inferior vena cava, tricuspid valve and right ventricle RV. The artificial valve 10 of certain embodiments is placed in the right ventricular outflow tract/pulmonary artery PA, while the artificial valve 10 of other embodiments is place at the position of the native valve. Any and all of the methods, operations, steps, etc. described herein can be performed on a living animal or on a non-living cadaver, cadaver heart, simulator, anthropomorphic ghost, analog, etc.

Multiple types of catheters can be used to deliver the artificial valve into the pulmonary trunk of a patient. Some embodiments use a balloon catheter where the valve is compressed around a balloon which expands the frame into the pulmonary trunk. Other embodiments will use a sheath catheter, which compresses the artificial valve into a sheath, and the frame expands on its own as it is removed from the sheath. In embodiments using a balloon catheter, the artificial valve may be compressed around a balloon, such as illustrated in FIG. 13.

Figure 13:
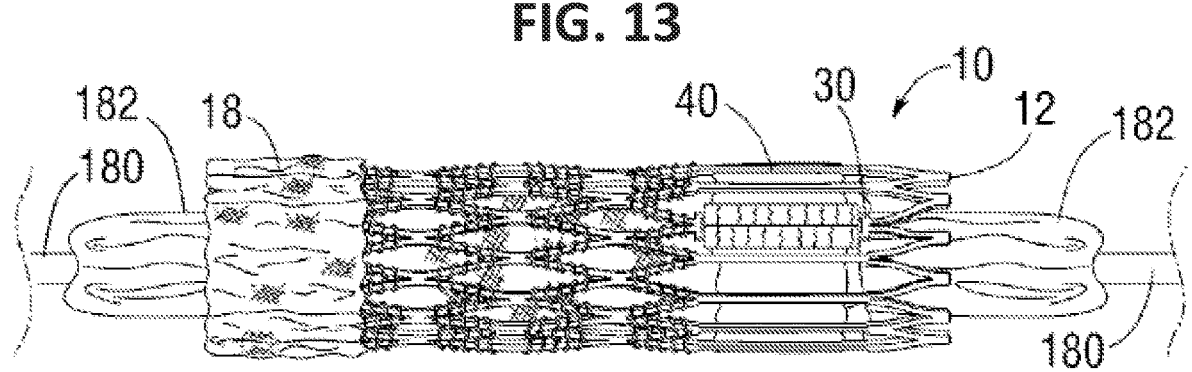
FIG. 13 illustrates an artificial heart valve in a compressed state and mounted on a balloon catheter in accordance with certain embodiments of the invention.

FIG. 13 shows an artificial valve 10 mounted on an elongated shaft 180 of a delivery apparatus, forming a delivery assembly for implanting the artificial valve 10 in a patient's body in accordance with various embodiments. The artificial valve 10 is mounted in a radially collapsed configuration for delivery into the body. The shaft 180 comprises an inflatable balloon 182 for expanding the balloon within the body, the crimped artificial valve 10 being positioned over the deflated balloon 182. As further shown, the artificial valve 10 comprises commissure portions of the leaflets extending radially outwardly through corresponding commissure window frames 30 to locations outside of the frame and sutured to the side struts of the commissure window frame 30. To minimize the crimp profile of the valve, the commissure window frames 30 can be depressed radially inwardly relative to the surrounding portions of the frame, such as the frame portions extending between adjacent commissure windows, when the valve is radially compressed to the collapsed configuration on the shaft 180. For example, the commissure window frames 30 of the frame can be depressed inwardly a radial distance of between about 0.2 mm and about 1 mm relative to the portions of the frame extending between adjacent commissure window frames 30 when the artificial valve 10 is radially collapsed. In this way, the outer diameter of the outflow end portion the valve comprising the commissure portions can be generally consistent, as opposed to the commissure portions jutting outward from the surrounding portions of the artificial valve 10, which could hinder delivery of the valve into the body. Even with the radially depressed commissure window frames 30, the outer diameter of the inflow end portion of the frame can still be smaller than, or about equal to, the outer diameter of the outflow end portion of the frame when the valve is radially collapsed on the shaft, allowing for a minimal maximum overall diameter of the valve. By minimizing the diameter of the valve when mounted on the delivery shaft, the assembly can contained within a smaller diameter catheter and thus can be passed through smaller vessels in the body and can be less invasive in general.

FIGS. 14A and 14B show cross sections of the compressed artificial valve 250 mounted on a balloon catheter. FIG. 14A illustrates an embodiment with a frame 202 having axially spaced struts 210 engineered to be relatively smaller in width, thus allowing spaces between struts 210 in a crimped configuration. In this configuration, the crimped artificial valve 250 will allow portions of the leaflets to protrude outwardly through the openings, as indicated by 216 on FIG. 14A. Because of this outward protrusion, the artificial valve 250 may be compressed into a smaller diameter than would normally exist. In comparison, a cross section of known artificial valves is demonstrated in FIG. 14B. In this embodiment, the struts are not engineered to have a smaller width, thus disallowing gaps and outward protrusion of the leaflets. As such, the outer diameter of the crimped artificial valve will be larger.

FIGS. 15A-15C show a prosthetic heart valve assembly 600 comprising an embodiment of a frame 602 for a prosthetic valve mounted on a balloon 606 of a delivery shaft 604. The frame 602 can be similar in shape to the cylindrical frame illustrated in FIG. 10A and can comprise an inflow end portion 610, an outflow end portion 612 and an intermediate portion 614. For clarity, the other components of the valve, such as the leaflets and the skirts, are not shown. The frame 602 can have a reduced thickness at the inflow end portion 610 and at the outflow end portion 612, relative to the thickness of the intermediate portion 614. Due to the thinner end portions, when the balloon 606 is inflated the end portions 610, 612 offer less resistance to expansion and expand faster than the intermediate portion 614, as shown in FIG. 15B. Because the end portions expand faster than the intermediate portion, the frame 602 becomes confined on the balloon 606, inhibiting the frame from sliding towards either end of the balloon and reducing the risk of the frame sliding off the balloon prematurely. As shown in FIG. 15C, further inflation of the balloon can cause the intermediate portion 614 of the frame to expand to the same final diameter as the end portions 610, 612 for implantation, after which the balloon can be deflated and removed. Controlling the position of the valve on the balloon can be important during delivery, especially with frames that foreshorten during expansion and move relative to the balloon. In the embodiment shown in FIGS. 15A-15C, the intermediate portion 614 of the frame can be held constant relative to the balloon while the two end portions foreshorten towards the intermediate portion due to the "dog-bone" effect of the balloon. Any conventional means can be used to produce the frame 602 with reduced thickness at the end portions 610, 612, such as sanding down the end portions with an abrasive, sand paper, or the like. In one embodiment, the end portions 610, 614 of the frame have a thickness of about 0.37 mm while the intermediate portion 614 has a thickness of about 0.45 mm.

Additional embodiments will use a sheath catheter to deploy artificial valves. FIGS. 16A-16E illustrate a distal portion of an exemplary embodiment of a catheter 3600 for delivering and deploying the artificial valve 10. The catheter 3600 can take a wide variety of different forms. In the illustrated example, the catheter 3600 includes an outer tube/sleeve 4910, an inner tube/sleeve 4912, an artificial valve connector 4914 that is connected to the inner tube 4912, and an elongated nosecone 28 that is connected to the artificial valve connector 4914 by a connecting tube 4916.

Figure 16A:
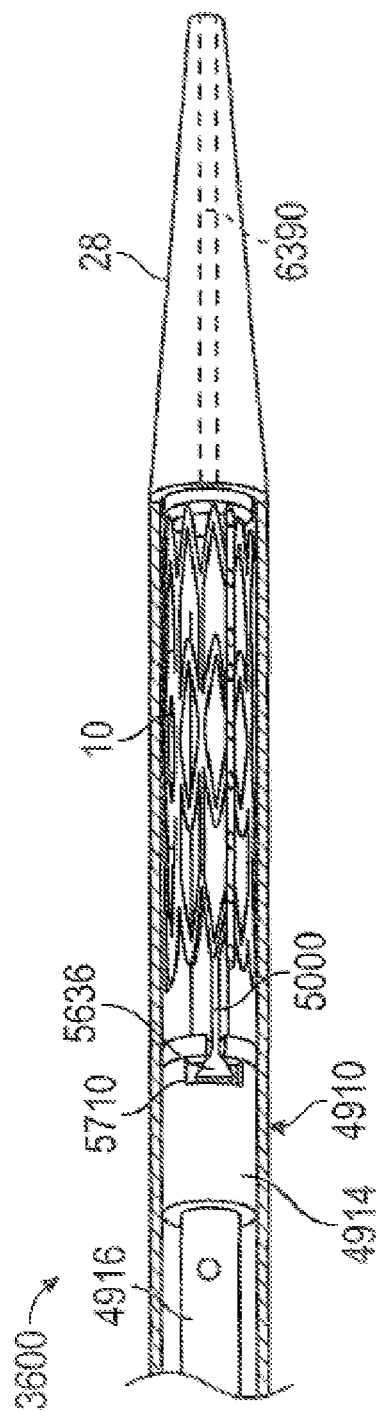
FIG. 16A-16E illustrate deployment of an exemplary embodiment of an artificial heart valve using a sheath catheter in accordance with certain embodiments of the invention.

The artificial valve 10 can be disposed in the outer tube/sleeve 4910 (See FIG. 16A). Elongated legs 5000 can connect the artificial valve 10 to the artificial valve connector 4914 (See FIG. 16A). The elongated legs 5000 can be retaining portions that are longer than the remainder of the retaining portions 414. The catheter 3600 can be routed over a guidewire 5002 to position the artificial valve 10 at the delivery site.

Figure 16B:
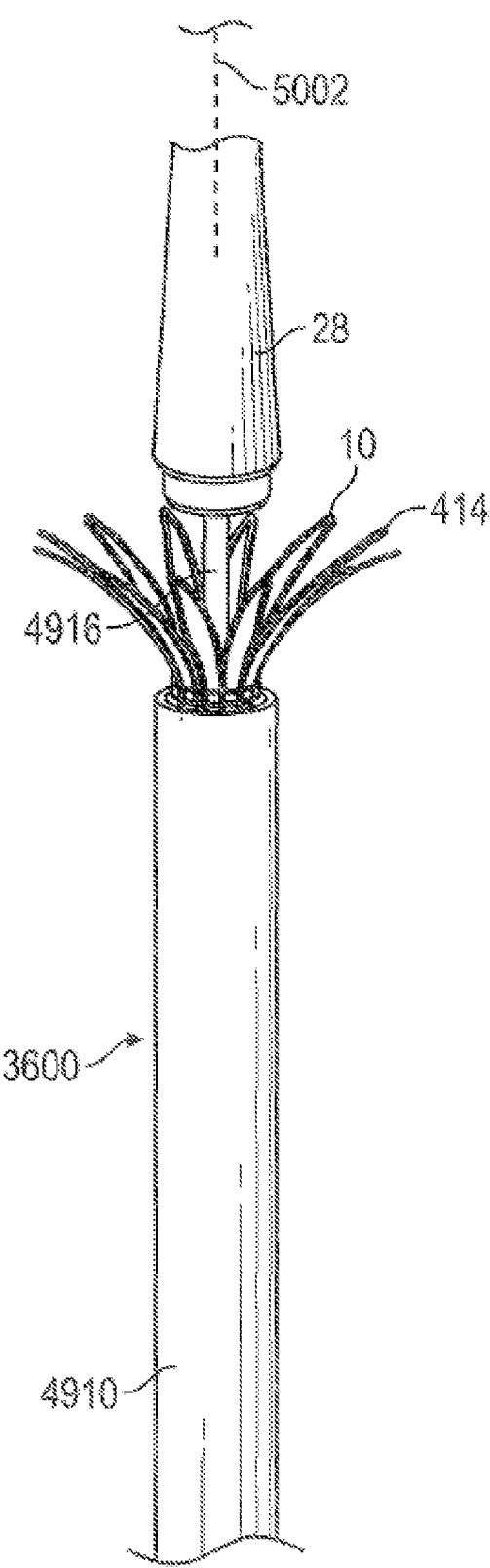
Figure 16C:
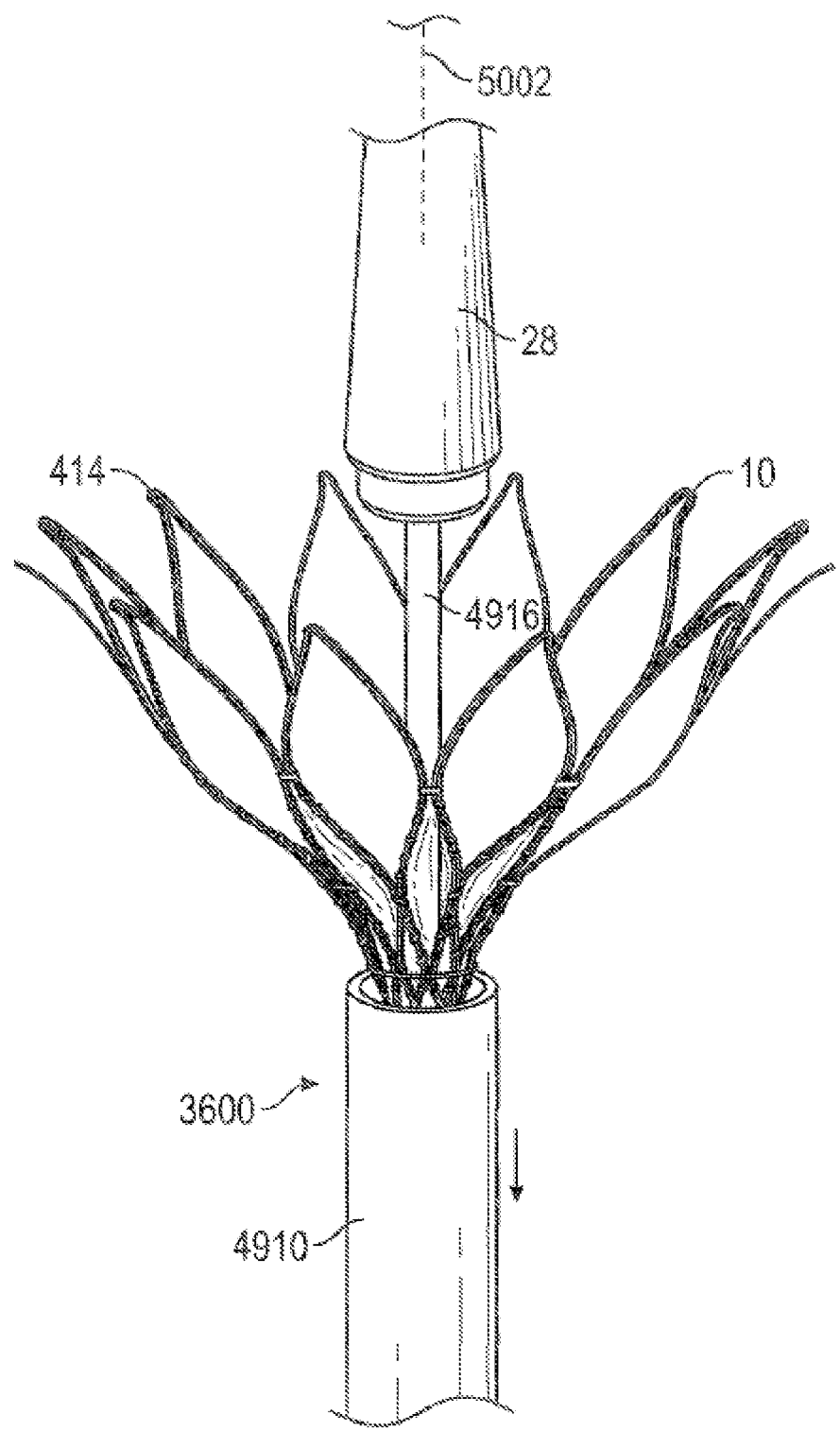
Figure 16D:
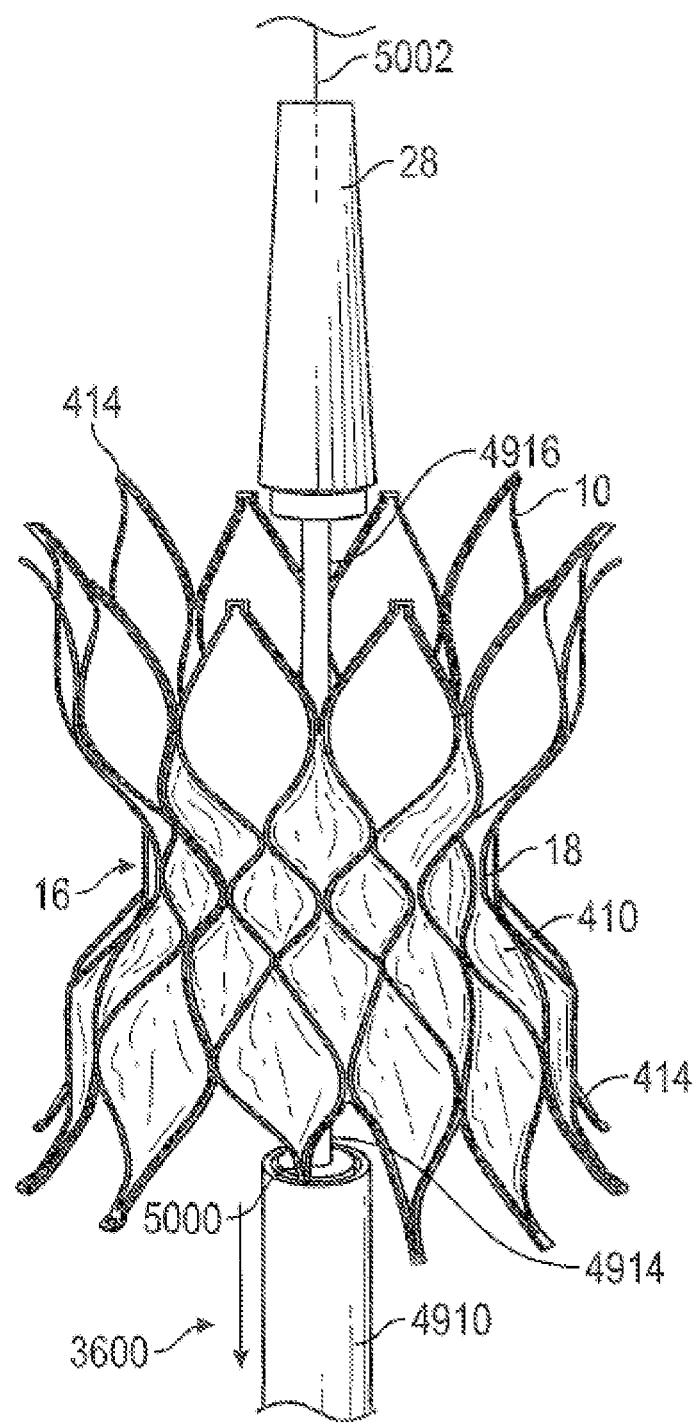
Figure 16E:
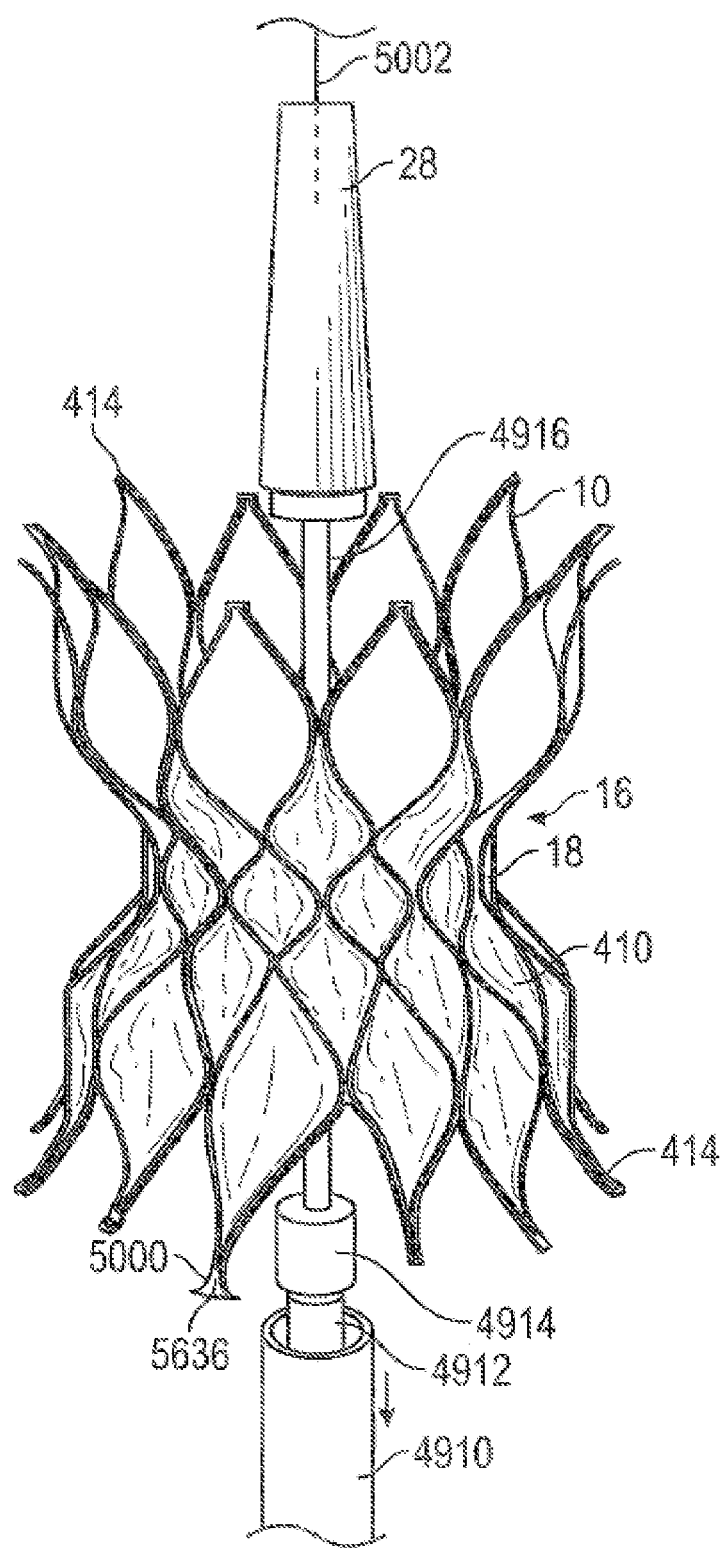

Referring to FIGS. 16B-16E, the outer tube 4910 is progressively retracted with respect to inner tube 4912, the artificial valve connector 4914, and the elongated nosecone 28 to deploy the artificial valve 10. In FIG. 16B, the artificial valve 10 begins to expand from the outer tube 4910. In FIG. 16C, a distal end 14 of the artificial valve 10 expands from the outer tube 4910. In FIG. 16D, the artificial valve 10 is expanded out of the outer tube, except the elongated legs 5000 remain retained by the artificial valve connector 4914 in the outer tube 4910. In FIG. 16E, artificial valve connector 4914 extends from the outer tube 4910 to release the legs 5000, thereby fully deploying the artificial valve. During deployment of an artificial valve in the circulatory system, similar steps may be used and the artificial valve may be deployed in a similar way.

DOCTRINE OF EQUIVALENTS

While the above description contains many specific embodiments, these should not be construed as limitations on the scope of the disclosure, but rather as an example of one embodiment thereof. Accordingly, the scope of the disclosure should be determined not by the embodiments illustrated, but by the appended claims and their equivalents.

What is claimed is:
1. An implantable artificial heart valve comprising:
 a frame having a longitudinal axis extending between an inflow end of the frame and an outflow end of the frame, the inflow end of the frame being configured to receive antegrade blood flowing into the prosthetic valve when implanted;

a leaflet structure positioned within the frame and constructed of a regenerative tissue;

an inner skirt positioned around an inner surface of the frame and extending along the longitudinal axis, wherein the inner skirt is constructed of a second regenerative tissue;

wherein the regenerative tissue and the second regenerative tissue are capable of being integrated into native tissue; and wherein the frame is comprised of a combination of bioabsorbable and non-bioabsorbable materials.

2. The implantable artificial heart valve of claim 1, wherein the bioabsorbable material is selected from the group consisting of: poly(L-lactide), poly(D-lactide), polyglycolide, poly(L-lactide-co-glycolide), polyhydroxyalkonate, polysaccharides, proteins, polyesters, polyhydroxyalkanoates, polyalkelene esters, polyamides, polycaprolactone, polylactide-co-polycaprolactone, polyvinyl esters, polyamide esters, polyvinyl alcohols, modified derivatives of caprolactone polymers, polytrimethylene carbonate, polyacrylates, polyethylene glycol, hydrogels, photo-curable hydrogels, terminal dials, poly(L-lactide-co-trimethylene carbonate), polyhydroxybutyrate; polyhydroxyvalerate, poly-orthoesters, poly-anhydrides, polyiminocarbonate, and copolymers and combinations thereof.

3. The implantable artificial heart valve of claim 1, wherein the leaflet structure and inner skirt are constructed of the same regenerative tissue.

4. The implantable artificial heart valve of claim 1, wherein the frame further comprises a plurality of commissure window frames to allow attachment of the leaflet structure.

5. The implantable artificial heart valve of claim 4, wherein the commissure window frames are constructed of the non-bioabsorbable material, and at least a portion of the frame is constructed of the bioabsorbable material.

6. The implantable artificial heart valve of claim 1, wherein the leaflet structure comprises a plurality of leaflets, each leaflet comprising a body portion having a free outflow edge, two opposing upper tabs extending from opposite sides of the body portion, and two opposing lower tabs, each lower tab extending from the body portion adjacent to a respective upper tab, the lower tabs extending from the body portion at opposite ends of the free outflow edge.

7. The implantable artificial heart valve of claim 6, wherein the lower tabs are folded about radially extending creases that extend radially from the opposite ends of the free outflow edge, such that a first portion of the lower tabs lies flat against the body portion of the respective leaflet, and the lower tabs are folded about axially extending creases such that a second portion of the lower tabs extends in a different plane than the first portion, wherein the radially extending creases and the axially extending creases are non-parallel.

8. The implantable artificial heart valve of claim 6, wherein the second portion of each lower tab is sutured to a respective upper tab.

9. The implantable artificial heart valve of claim 1, wherein the frame is radially collapsible to a collapsed configuration and radially expandable to an expanded configuration.

10. The implantable artificial heart valve of claim 1, wherein the frame further comprises tissue engaging elements to allow fixation of the artificial heart valve to the wall of a blood vessel.

11. The implantable artificial heart valve of claim 10, wherein the tissue engaging elements include a bioabsorbable glue to prevent the tissue engaging elements from expanding and allowing the artificial heart valve to be repositioned.

12. The implantable artificial heart valve of claim 1, wherein the regenerative tissue and second regenerative tissue are selected from the group consisting of: polyglactin, collagen, and polyglycolic acid.

13. The implantable artificial heart valve of claim 12, wherein the regenerative tissue further comprises extracellular matrix proteins selected from the group consisting of: hydroxyproline, vitronectin, fibronectin and collagen type I, collagen type III, collagen type IV, collagen VI, collagen XI, collagen XII, fibrillin I, tenascin, decorin, byglycan, versican, asporin, and combinations thereof.

14. The implantable artificial heart valve of claim 1, wherein the inner skirt extends beyond at least one of the outflow end and inflow end of the frame and forms an outer skirt attached to an outer surface of the frame.

15. The implantable artificial heart valve of claim 1, wherein the frame further comprises growth factors to promote integration of the regenerative tissue.

16. The implantable artificial heart valve of claim 1, wherein an outer diameter of the inflow end portion of the frame is smaller than an outer diameter of the outflow end portion of the frame.

17. The implantable artificial heart valve of claim 1, wherein the frame has a plurality of openings and portions of the leaflet structure protrude through the openings while the prosthetic valve is in a radially collapsed configuration.

18. The implantable artificial heart valve of claim 1, wherein the regenerative tissue and second regenerative tissue are decellularized tissue.

19. The implantable artificial heart valve of claim 1, wherein one or more of the frame, the regenerative tissue, and the second regenerative tissue incorporate a growth factor.

20. The implantable artificial heart valve of claim 19, wherein the growth factor is selected from the group consisting of: transforming growth factor alpha (TGF-alpha), transforming growth factor beta (TGF-beta), basic fibroblast growth factor (bFGF), vascular epithelial growth factor (VEGF), and combinations thereof.

* * * * *